United States Patent
Freund et al.

(10) Patent No.: US 12,229,947 B2
(45) Date of Patent: Feb. 18, 2025

(54) OCT-BASED RETINAL ARTERY/VEIN CLASSIFICATION

(71) Applicant: Carl Zeiss Meditec Inc, Dublin, CA (US)

(72) Inventors: Kenneth Bailey Freund, New York, NY (US); Xiaoyu Xu, Guangzhou (CN); Mary K. Durbin, San Francisco, CA (US)

(73) Assignee: Carl Zeiss Meditec Inc., Dublin, CA (US)

( * ) Notice: Subject to any disclaimer, the term of this patent is extended or adjusted under 35 U.S.C. 154(b) by 0 days.

(21) Appl. No.: 16/886,758

(22) Filed: May 28, 2020

(65) Prior Publication Data

US 2020/0394789 A1     Dec. 17, 2020

Related U.S. Application Data

(60) Provisional application No. 62/860,660, filed on Jun. 12, 2019.

(51) Int. Cl.
    *G06T 7/00*          (2017.01)
    *A61B 3/10*          (2006.01)

(52) U.S. Cl.
    CPC ............ *G06T 7/0012* (2013.01); *A61B 3/102* (2013.01); *G06T 2207/10028* (2013.01);
(Continued)

(58) Field of Classification Search
    CPC ......... G06T 7/0012; G06T 2207/30041; G06T 2207/10101; G06T 2211/404;
(Continued)

(56) References Cited

U.S. PATENT DOCUMENTS

| | | | |
|---|---|---|---|
| 4,170,398 A | 10/1979 | Koester | |
| 4,732,466 A | 3/1988 | Humphrey | |

(Continued)

FOREIGN PATENT DOCUMENTS

| | | |
|---|---|---|
| WO | WO-2012059236 A1 | 5/2012 |
| WO | WO-2016124644 A1 | 8/2016 |

OTHER PUBLICATIONS

Son, Taeyoon, et al. "Near infrared oximetry-guided artery-vein classification in optical coherence tomography angiography." Experimental Biology and Medicine 244.10 (2019): 813-818. https://journals.sagepub.com/doi/full/10.1177/1535370219850791 (Year: 2019).*

(Continued)

*Primary Examiner* — Wesley J Tucker
*Assistant Examiner* — Han Hoang
(74) *Attorney, Agent, or Firm* — Snell & Wilmer L.L.P.

(57) ABSTRACT

An optical coherence tomography (OCT) unit provides a mechanism/method for automatic artery and vein identification. The method may be embodied by specialized algorithm or by a machine learning model, such as a support vector machine or neural network. The present method may identify a vascular configuration that forms a vortex structure in the deep capillary plexus (DCP) of an OCT-based (e.g., OCTA) image of a retina. The identified vortex may then be designated a vein, and other vascular structures from other plexuses, such as from the superficial vascular plexus (SVP), that connect to the identified vortex structure are likewise designated veins. Additional criteria, some based on the vein designations, may be used to identify arteries.

25 Claims, 24 Drawing Sheets
(13 of 24 Drawing Sheet(s) Filed in Color)

(52) U.S. Cl.
CPC ............... *G06T 2207/10101* (2013.01); *G06T 2207/20081* (2013.01); *G06T 2207/20084* (2013.01); *G06T 2207/30041* (2013.01); *G06T 2207/30101* (2013.01); *G06T 2211/404* (2013.01)

(58) Field of Classification Search
CPC . G06T 2207/30101; G06T 2207/20081; G06T 2207/20084; G06T 2207/10028; A61B 3/102; A61B 3/1241; A61B 3/1233
See application file for complete search history.

(56) References Cited

U.S. PATENT DOCUMENTS

| | | | |
|---|---|---|---|
| 6,549,801 B1 | 4/2003 | Chen et al. | |
| 6,741,359 B2 | 5/2004 | Wei et al. | |
| 7,301,644 B2 | 11/2007 | Knighton et al. | |
| 8,967,806 B2 | 3/2015 | Bublitz et al. | |
| 8,998,411 B2 | 4/2015 | Tumlinson et al. | |
| 9,332,902 B2 | 5/2016 | Tumlinson et al. | |
| 9,456,746 B2 | 10/2016 | Bublitz et al. | |
| 9,700,206 B2 | 7/2017 | An et al. | |
| 9,706,915 B2 | 7/2017 | Everett | |
| 9,759,544 B2 | 9/2017 | An et al. | |
| 2005/0171438 A1 | 8/2005 | Chen et al. | |
| 2010/0027857 A1 | 2/2010 | Wang | |
| 2010/0195893 A1* | 8/2010 | Fuchigami | A61B 5/02007 382/132 |
| 2012/0277579 A1 | 11/2012 | Sharma et al. | |
| 2012/0307014 A1 | 12/2012 | Sharma et al. | |
| 2014/0232987 A1 | 8/2014 | Westphal et al. | |
| 2015/0131050 A1 | 5/2015 | Bublitz et al. | |

OTHER PUBLICATIONS

Campbell, J. P., et al. "Detailed vascular anatomy of the human retina by projection-resolved optical coherence tomography angiography." Scientific reports 7.1 (2017): 1-11. https://www.nature.com/articles/srep42201 (Year: 2017).*

Girard, Fantin, and Farida Cheriet. "Artery/vein classification in fundus images using CNN and likelihood score propagation." 2017 IEEE Global Conference on Signal and Information Processing (GlobalSIP). IEEE, 2017. https://ieeexplore.jeee.org/abstract/document/8309054 (Year: 2017).*

Hirano, Takao, et al. "Distinct retinal capillary plexuses in normal eyes as observed in optical coherence tomography angiography axial profile analysis." Scientific reports 8.1 (2018): 1-7. https://www.nature.com/articles/s41598-018-27536-5 (Year: 2018).*

Nesper, Peter L., and Amani A. Fawzi. "Human parafoveal capillary vascular anatomy and connectivity revealed by optical coherence tomography angiography." Investigative ophthalmology & visual science 59.10 (2018): 3858-3867. https:// iovs.arvojournals.org/article.aspx?articleid=2696444 (Year: 2018).*

Alam et al., (2018). "Color Fundus Image Guided Artery-Vein Differentiation in Optical Coherence Tomography Angiography," Invest Ophthalmol Vis Sci, 59:4953-4962.

Alam et al., (2019). "OCT feature analysis guided artery-vein differentiation in OCTA," Biomedical Optics Express, 10:2055-2066.

Balaratnasingam et al., (2018). "Comparisons Between Histology and Optical Coherence Tomography Angiography of the Periarterial Capillary-Free Zone," Am J Ophthalmol, 189:55-64.

Blazkiewicz et al., (2005). "Signal-to-noise ratio study of full-field Fourier-domain optical coherence tomography," Applied Optics, 44(36):7722-7729.

Foreman et al., (1996). "Three dimensional analysis of the retinal vasculature using immunofluorescent staining and confocal laser scanning microscopy," Br J Ophthalmol, 80:246-51.

Foulds et al., (2010). "A porcine model of selective retinal capillary closure induced by embolization with fluorescent microspheres," Invest Ophthalmol Vis Sci, 51:6700-9.

Freund et al., (2018). "Association of Optical Coherence Tomography Angiography of Collaterals in Retinal Vein Occlusion With Major Venous Outflow Through the Deep Vascular Complex," JAMA Ophthalmol, 136:1262-1270.

Garrity et al., (2017). "Considerations in the Understanding of Venous Outflow in the Retinal Capillary Plexus," Retina, 37:1809-1812.

Gattoussi et al., (2017). "Correlating structural and angiographic optical coherence tomography in the intermediate and deep retinal capillary plexuses," Exp Eye Res, 165:96-98.

Genevois et al., (2004). "Microvascular remodeling after occlusion-recanalization of a branch retinal vein in rats," Invest Ophthalmol Vis Sci, 45:594-600.

Gu Bet al., (2018). "Noninvasive in vivo characterization of erythrocyte motion in human retinal capillaries using high-speed adaptive optics near-confocal imaging," Biomed Opt Express, 9:3653-3677.

Hagag et al., (2017). "Optical coherence tomography angiography: Technical principles and clinical applications in ophthalmology," Taiwan J Ophthalmol, 7:115-129.

Hillmann et al., (2011). "Holoscopy—holographic optical coherence tomography," Optics Letters, 36(13):2390-2.

Ikram et al., (2006). "Retinal vessel diameters and cerebral small vessel disease: the Rotterdam Scan Study," Brain, 129:182-8.

Iwase et al., (2015). "Differences of Retinal Blood Flow Between Arteries and Veins Determined by Laser Speckle Flowgraphy in Healthy Subjects," Medicine, 94:e1256, 8 pages.

Kashani et al., (2017). "Optical coherence tomography angiography: A comprehensive review of current methods and clinical applications," Prog Retin Eye Res, 60:66-100.

Kondermann et al., (2007). "Blood vessel classification into arteries and veins in retinal images," Medical Imaging: SPIE, 651247, 9 pages.

McLeod et al., (2010). "Krogh cylinders in retinal development, panretinal hypoperfusion and diabetic retinopathy," Acta Ophthalmol, 88:817-35.

Nakamura et al., (2007). "High-Speed three dimensional human retinal imaging by line field spectral domain optical coherence tomography," Optics Express, 15(12):7103-7116.

Ouyang et al., (2014). "An easy method to differentiate retinal arteries from veins by spectral domain optical coherence tomography: retrospective, observational case series," BMC Ophthalmol, 14:66, 9 pages.

Pappuru et al., (2012). "Clinical significance of B-scan averaging with SD-OCT," Ophthalmic Surg Lasers Imaging, 43:63-8.

Paques et al., (2003). "Structural and hemodynamic analysis of the mouse retinal microcirculation," Invest Ophthalmol Vis Sci, 44:4960-7.

Qiu et al., (2009). "Sigurdsson S, et al. Microvascular lesions in the brain and retina: The age, gene/environment susceptibility—Reykjavik study," Ann Neurol, 65:569-76.

Shao et al., (2016). "Retinal vessel diameter changes in different severities of diabetic retinopathy by SD-OCT," Eur J Ophthalmol, 26:342-6.

Shin et al., (2018). "Optical coherence tomography angiography analysis of changes in the retina and the choroid after haemodialysis," Sci Rep, 8:17184, 10 pages.

Son et al., (2019). "Artery and vein differentiation in retinal optical coherence tomography angiography of macular region," Proc. SPIE 10858, Ophthalmic Technologies XXIX, 108581L, 7 pages.

Spaide (2015). "Retinal vascular layers imaged by fluorescein angiography and optical coherence tomography angiography," JAMA Ophthalmol, 133:45-50.

Spaide et al., (2015). "Image Artifacts in Optical Coherence Tomography Angiography," Retina, 35:2163-80.

Spaide et al., (2017). "Evaluation of Segmentation of the Superficial and Deep Vascular Layers of the Retina by Optical Coherence Tomography Angiography Instruments in Normal Eyes," JAMA Ophthalmol, 135:259-262.

(56) References Cited

OTHER PUBLICATIONS

Suzuki, (1995). "Direct measurement of retinal vessel diameter: comparison with microdensitometric methods based on fundus photographs," Surv Ophthalmol, 39:S57-S65.
Tan et al., (2018). "An overview of the clinical applications of optical coherence tomography angiography," Eye, 32:262-286.
Wang et al., (2011). "Pilot study of optical coherence tomography measurement of retinal blood flow in retinal and optic nerve diseases," Invest Ophthalmol Vis Sci, 52:840-5.
Welikala et al., (2017). "Automated arteriole and venule classification using deep learning for retinal images from the UK Biobank cohort," Comput Biol Med, 90:23-32.
Wong et al, (2003). "The prevalence and risk factors of retinal microvascular abnormalities in older persons: The Cardiovascular Health Study," Ophthalmology, 110:658-66.
Zhang et al., (2016). "Projection-resolved optical coherence tomographic angiography," Biomed Opt Express, 7:816-28.
Zheng et al., (2019). "Age-Dependent Changes in the Macular Choriocapillaris of Normal Eyes Imaged with Swept-Source OCT Angiography," Am J Ophthalmol, 200:P110-122, 32 pages.

\* cited by examiner

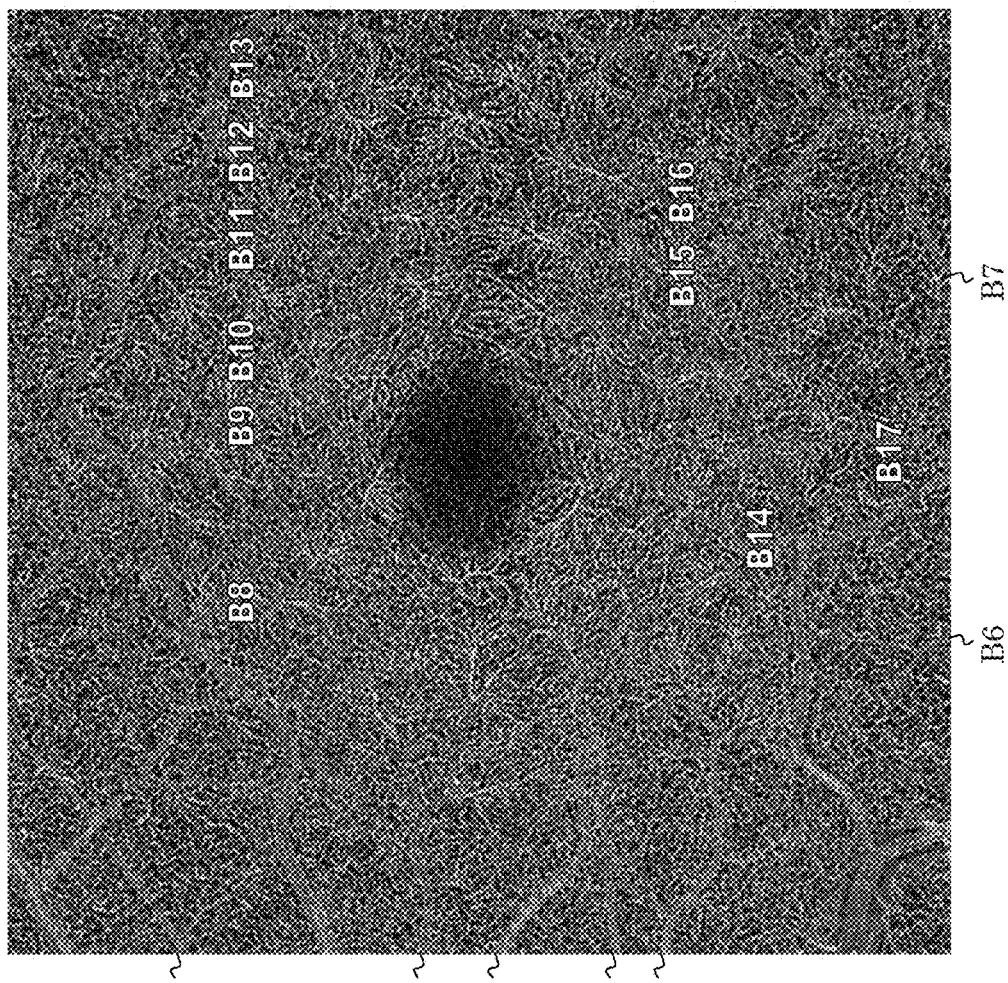
FIG. 6B
FIG. 6A

Table 1. Average Grading Accuracy in Each Stage Subdivided into Scanning Patterns (Mean ± Standard Deviation; %) and Comparisons

| Scanning Pattern | Stage 1 | Stage 2 | Stage 3 | p value[a] |
|---|---|---|---|---|
| 3x3 mm | 49.9 ± 16.3 | 79.2 ± 9.6 | 96.9 ± 3.1 | < 0.001 |
| 6x6 mm | 51.4 ± 20.8 | 72.3 ± 7.9 | 93.2 ± 3.3 | < 0.001 |
| Total | 50.4 ± 17.0 | 75.4 ± 6.0 | 94.7 ± 2.6 | < 0.001 |
| p value[b] | 0.850 | 0.020 | 0.029 | / |

[a] Comparisons of the grading accuracy between the 3 stages in each scanning pattern using generalized estimating equations.
[b] Comparisons of the grading accuracy between 3x3 mm scan and 6x6 mm scan in each stage using generalized estimating equations.

FIG. 11

Table 2. Sensitivity and Specificity in Classifying Retinal Veins in Each Stage Subdivided into Scanning Patterns (%)

| Scanning Pattern | Stage 1 | | Stage 2 | | Stage 3 | |
|---|---|---|---|---|---|---|
| | Sensitivity | Specificity | Sensitivity | Specificity | Sensitivity | Specificity |
| 3x3 mm | 44.96 | 56.73 | 72.77 | 87.68 | 94.37 | 94.12 |
| 6x6 mm | 44.77 | 60.00 | 74.93 | 67.88 | 91.71 | 95.52 |
| Total | 44.85 | 58.37 | 74.14 | 78.22 | 92.62 | 94.82 |

FIG. 12

Table 3. Correlations of Grading Accuracy with Grading Time in Each Stage

| | Stage 1 | Stage 2 | Stage 3 |
|---|---|---|---|
| $r$ | -0.013 | 0.518 | -0.164 |
| 95% confidence interval of $r$ | -0.624 – 0.679 | 0.057 – 0.970 | -0.798 – 0.741 |
| $p$ value | 0.974 | 0.189 | 0.674 |

FIG. 13A

Table 4. Correlations of Grading Accuracy with Graders' Years in Practicing Ophthalmology in Each Stage Subdivided into Scanning Patterns

| | Stage 1 | | Stage 2 | | Stage 3 | |
|---|---|---|---|---|---|---|
| | 3x3 mm | 6x6 mm | 3x3 mm | 6x6 mm | 3x3 mm | 6x6 mm |
| $r$ | 0.587 | 0.608 | 0.275 | 0.005 | 0.579 | 0.617 |
| 95% confidence interval of $r$ | -0.498 – 0.926 | -0.322 – 0.902 | -0.354 – 0.663 | -0.670 – 0.706 | -0.008 – 0.920 | 0.032 – 0.930 |
| P value | 0.097 | 0.082 | 0.474 | 0.990 | 0.103 | 0.077 |

FIG. 13B

OCT-BASED RETINAL ARTERY/VEIN CLASSIFICATION

PRIORITY

The present application claims priority to Provisional Application Ser. No. 62/860,660 filed Jun. 12, 2019, the contents of which are hereby incorporated by reference in their entirety.

FIELD OF INVENTION

The present invention is generally directed to the field of ophthalmic imaging systems. More specifically, it is directed to techniques for identifying arterial and venous systems in images of retinal vasculature. Still more specifically, it is directed to techniques for classification of retinal vessels as arteries or veins in optical coherence tomography images irrespective of whether the optic nerve is not within the image.

BACKGROUND

There are various types of ophthalmic examination systems, including ophthalmoscopes, optical coherence tomography, and other ophthalmic imaging systems (see for example U.S. Pat. Nos. 4,170,398, 4,732,466, PCT Publication No. 2012059236, US Patent Application No. 2014/0232987, and US Patent Publication No. 2015/0131050). Theses imaging technologies may provide high-resolution, in vivo imaging of the human retina and its vasculature, which is generally comprised of arteries and veins. To make better diagnostic use of these images, it is beneficial to distinguish between arteries and veins within the images of retinal vasculature. Structurally, arteries and veins are very similar, but differ in their function. Arteries carry oxygenated blood away from the heart to the body, and veins carry oxygen-poor blood back from the body to the heart.

Retinal blood vessels are the only visible and optically accessible small blood vessels in the human body that can be imaged in vivo and noninvasively. Since the arterial and venous systems are differently affected in many systemic and retinal vascular diseases, classification of retinal vessels as arteries or veins is of high medical interest. A fuller discussion of how arteries and veins may be affected differently by different deceases is found in "Microvascular lesions in the brain and retina: The age, gene/environment susceptibility-Reykjavik study" by Qiu C. et al., *American Neurological Association*, 2009; 65:569-76, and in "The prevalence and risk factors of retinal microvascular abnormalities in older persons: The Cardiovascular Health Study", by Wong T. Y. et al., *American Academy of Ophthalmology*, 2003; 110:658-66.

In high quality color fundus photographs, arteries can be distinguished from veins by using various characteristics such as size, shape, vessel crossing patterns, color, brightness, and optical reflexes. Understanding that arteries and veins usually alternate near the optic nerve head also aids in accurate vessel classification. A discussion of techniques for distinguishing between arteries and veins in high quality color fundus photographs is provided in "Blood vessel classification into arteries and veins in retinal images," by Kondermann C et al., *Medical Imaging: SPIE*, 2007:9, and in "Automated arteriole and venule classification using deep learning for retinal images from the UK Biobank cohort" by Welikala R. A. et al., *Computers Biology and Medicine*, 2017; 90:23-32. In clinical practice, however, fundus photographs are often inadequate to classify the smaller caliber vessels, particularly in eyes with media opacities or other pathology obscuring differentiating features.

Fluorescein angiography (FA) may also be used to identify arteries and veins in retinal vasculature. In an FA examination, a series of time-lapse images are captured after injecting a light-reactive dye (e.g., fluorescent dye) into a subject's bloodstream. It is noted that care must be taken since the fluorescent dye may lead to a life-threatening allergic reaction in a portion of the population. High contrast, greyscale images are captured using specific light frequencies selected to excite the dye. As the dye flows through the eye, various portions of the eye are made to glow brightly (e.g., fluoresce), making it possible to discern the progress of the dye, and hence the blood flow, through the eye. To reliably distinguish arteries from veins on greyscale FA images, a review of images with precise transit phase (usually within several seconds and with obvious individual variation) is needed. Furthermore, if the transit phase is lost, or if blood vessel classification in both eyes is needed, a repeated FA examination is required on a subsequent day, which is impractical in many real-world situations. Because FA is an invasive procedure, it is rarely used as a primary method for classifying retinal vessels.

Optical coherence tomography (OCT) provides volumetric, structural, vascular images, and OCT angiography (OCTA) provides volumetric, functional, vascular images that identify areas of blood flow. In both OCT and OCTA, two-dimensional, en face images may be generated from their volumetric data. Although OCTA can identify regions of blood flow, it generally cannot identify the direction of blood flow. Previously, several OCT-based strategies for distinguishing arteries and veins have been developed. In one approach (disclosed in "Pilot study of optical coherence tomography measurement of retinal blood flow in retinal and optic nerve diseases," by Wang Y. et al., *Invest Ophthalmol Vis Sci*, 2011; 52:840-5), laboratory based Doppler Fourier-domain (FD) OCT was used to measure and compare the flow velocity in arterial and venous systems. This technique was found to be time-consuming and of limited utility in routine clinical care. Later, by measuring the vessel diameter and wall thickness, and assessing the presence or absence of the hyperreflective lower border reflectivity feature using commercially available spectral domain OCT (SD-OCT), retinal vessel classification became less cumbersome yet still needed additional scans targeting the vessels of interests (see for example, Ouyang Y. et al., "An easy method to differentiate retinal arteries from veins by spectral domain optical coherence tomography: retrospective, observational case series," *BMC Ophthalmol*, 2014; 14:66). Another approach combined laser speckle flowgraphy (LSFG), a technique used to measure relative retinal and choroidal blood flow velocities, with an adaptive optics (AO) camera imaging fine retinal vasculature structure to determine retinal vessel types (as discussed in "Differences of Retinal Blood Flow Between Arteries and Veins Determined by Laser Speckle Flowgraphy in Healthy Subjects" by Iwase T et al., *Medicine (Baltimore)*, 2015; 94:e1256). Still another approach used a custom-built, high-speed, AO, near-confocal imaging device to show that imaging erythrocyte motion in living human eyes could facilitate accurate classification of vessels at the level of retinal microcirculation (see "Noninvasive in vivo characterization of erythrocyte motion in human retinal capillaries using high-speed adaptive optics near-confocal imaging" by Gu B. et al., *Biomed Opt Express*, 2018; 9:3653-3677). This approach, however, is not commercially available and is generally limited to research facilities. Thus, none of these methods allow for immediate visual evaluation of retinal vessel classification without additional scans, and many of them cannot currently be used in clinical practice due to delivery barriers.

OCTA has many well-established ophthalmic diagnostic uses, and it may be combined with other imaging modalities, such as color fundus images, to enhance its diagnostic capabilities. For example, a technique for improving OCTA detection and staging of diabetic retinopathy (DR) is described in "Color Fundus Image Guided Artery-Vein Differentiation in Optical Coherence Tomography Angiography," by Alam M. et al., *Invest Ophthalmol Vis Sci*, 2018; 59:4953-4962. This technique uses color fundus images to guide OCTA artery/vein differentiation.

It is an object of the present invention to provide tools to facilitate the classification of retinal vasculature into arterial and venous systems.

It is another object of the present invention to provide a mechanism to fully, or partially, automate the identification of arteries and veins within retinal vasculature without the need for well-known landmark sources of blood vessels, such as the optic nerve head.

It is a further object of the present invention to provide methods of directly identifying arteries and veins in OCT-based images, which may have a limited field-of-view, without the use of color fundus images.

SUMMARY OF INVENTION

The above objects are met in a method/system for facilitating the classification of arteries and veins in optical coherence tomography (OCT)-based data, such as images based on OCT structural data and/or images based on OCT angiography (OCTA) data. Herein is presented a method and system for rapid and reliable identification of retinal arteries and veins in OCT-based data, such as standard en face images, which may be acquired on commercially available OCT/OCTA devices. The present method/system may incorporate the use of vortices (e.g., local configurations/regions of vortex-like structures and/or local configurations/regions of vascular convergence) in the deep capillary plexus (DCP) to identify venous origin. For example, the present invention provides various methods of identifying (e.g., capillary) vortices (e.g., reference vascular regions of predefined structural configuration) in the DCP and using these vortices (e.g., reference vascular regions) as anatomic biomarkers of venous origin.

OCT-based imaging can resolve the discrete capillary plexuses within the retina. For example, the ability of OCTA to provide depth-resolved images of retinal and choroidal vascular blood flow without the need for intravenous dye has made it a widely used imaging tool for studying retinal and optic nerve disorders including neovascular age-related macular degeneration, retinal vascular diseases, macular telangiectasia, pathological myopia, inflammatory chorioretinal diseases, and glaucoma. Fast scanning speeds, improved retinal layer segmentation, and projection artifact removal algorithms have further enhanced current OCT devices to resolve the discrete capillary plexuses within the retina.

The present method/system may use one or more computing devices, e.g., electronic processor(s), to implement multiple image processing algorithms or machine learning models (e.g., support vector machines or (e.g., deep learning) neural networks) that analyze OCT-based data (e.g., A-scans, B-scans, C-scans, en face images of OCT/OCTA slabs (depth en-coded and/or non-depth encoded)) to extract vascular structures from the OCT-based data and identify/classify individual vascular structures as venous or arterial vascular structures. For example, the present method/system may start by obtaining (e.g., capturing/collecting) OCT data (e.g. OCT structural data and/or OCT angiography data), and extracting depth information from the OCT data, including a first vascular plexus at a first depth and a second vascular plexus at a second depth deeper than the first depth. For example, the first vascular plexus may be the superficial vascular plexus (SVP) and the second vascular plexus may be the deep vascular complex (DVC), which may include the intermediate capillary plexus (ICP) and/or the deep capillary plexus (DCP). The vascular configurations of the second vascular plexus are analyzed to identify regions having a predefined structural configuration. For example, local regions having a vortex structural configuration or local regions of vascular convergence are identified and designated as reference vascular regions. It is herein put forth that these structural configurations are characteristic of venous blood drainage and correspond to venous structures. A first vascular structure in the first vascular plexus is then given a venous designation or arterial designation based on its relation to the identified reference vascular region(s). For example, if the first vascular structure has a vascular connection to a reference vascular region, then the first vascular structure is assigned a venous designation. Alternatively, if the first vascular structure does not have a vascular connection to a reference vascular region but is adjacent to another vascular structure in the first vascular plexus that does have a vascular connection to a reference vascular region, then the first vascular structure is assigned an arterial designation.

The process may be fully or partly automated. An example of a partly automated process would be if the present method/system identifies the reference vascular region(s) and labels the region(s) on a display of the OCT data. A technician may then use the identified reference vascular region(s) to discern whether a specific vascular structure is a vein or an artery. In a fully automated process, the present method/system may identify vascular structures, and assign their venous or arterial designations directly. In another example, a technician may be presented with an image of the OCT data (e.g., on an electronic display), and the technician may select one or more vascular structures, such as by use of an electronic input device (e.g., touch screen, computer mouse, keyboard, etc.). The present system may then respond by labeling the selected vascular structures as veins or arteries.

Other objects and attainments together with a fuller understanding of the invention will become apparent and appreciated by referring to the following description and claims taken in conjunction with the accompanying drawings.

Several publications may be cited or referred to herein to facilitate the understanding of the present invention. All publications cited or referred to herein, are hereby incorporated herein in their entirety by reference.

The embodiments disclosed herein are only examples, and the scope of this disclosure is not limited to them. Any embodiment feature mentioned in one claim category, e.g. system, can be claimed in another claim category, e.g. method, as well. The dependencies or references back in the attached claims are chosen for formal reasons only. However, any subject matter resulting from a deliberate reference back to any previous claims can be claimed as well, so that any combination of claims and the features thereof are disclosed and can be claimed regardless of the dependencies chosen in the attached claims.

BRIEF DESCRIPTION OF THE DRAWINGS

The patent or application file contains at least one drawing executed in color. Copies of this patent or patent application publication with color drawings will be provided by the Office upon request and payment of the necessary fee.

In the drawings wherein like reference symbols/characters refer to like parts:

FIGS. 3A, 4A, 5A, and 6A are 3×3 mm images, each of which may be part of an image set, which may constitute part (or a whole) of a training/testing set.

FIGS. 3B, 4B, 5B and 6B are 6×6 mm images, each of which includes at least part of a corresponding 3×3 mm image from FIGS. 3A, 4A, 5A, and 6A, respectively, and which (with its respective 3×3 mm image) may be part of an image set that may constitute part (or a whole) of a training/testing set. Vessels that need to be classified as arteries or veins are identified (e.g., numbered) on each image, or slab.

FIG. 11 provides a Table 1, which summarizes the overall grading accuracy and the separate accuracies for the 3×3 mm and 6×6 mm image sets at each training stage.

FIG. 12 provides a Table 2, which shows the sensitivity and specificity for identifying retinal veins at each stage.

FIG. 13A provides Table 3, which shows the correlation between grading accuracy and mean time spent on each vessel during each training stage.

FIG. 13B provides a Table 4, which shows the correlations between grading accuracy at each training stage and the graders' mean years in practice subdivided by scan pattern size.

DESCRIPTION OF THE PREFERRED EMBODIMENTS

As is discussed more fully below, optical coherence tomography (OCT) and optical coherence tomography angiography (OCTA) enable noninvasive, depth-resolved (e.g., A-scan), volumetric (e.g., C-scan) and two-dimensional (e.g., en face or cross-sectional/B-scan) visualization of retinal vasculature. OCT provides structural images of vasculature whereas OCTA provides functional images of vasculature. For example, OCTA may image vascular flow by using the motion of flowing blood as an intrinsic contrast. However, there are various types of ophthalmic imaging systems, such as discussed below in section "Fundus Imaging System" and in section "Optical Coherence Tomography (OCT) Imaging System." Unless otherwise stated, aspects of the present invention(s) may apply to any, or all, such ophthalmic imaging systems. For example, the methods/systems presented herein for differentiating arteries and veins in vasculature images may be applied to OCT structural images and/or OCTA functional images.

As is discussed in more detail below, Applicants have found a method/system that, at least in part, may make use of images of capillary plexuses to differentiate arteries from veins in retinal vasculature. OCTA is currently a preferred modality for imaging capillary plexuses. Consequently, for ease of discussion, the below-described embodiments may be illustratively shown as applied to OCTA images, but it to be understood that the presented embodiments may also be applied to OCT (structural) images or other depth-resolved ophthalmic images, particularly those that show discrete capillary plexuses. For example, Freund et al, "Correlating structural and angiographic optical coherence tomography in the intermediate and deep retinal capillary plexuses," Elsevier publishing, *Experimental Eye Research*, Vol. 165, 2017, pages 96-98, herein incorporated in its entirety by reference, describe the use of OCTA and structural OCT to image different plexus layers, including the intermediate capillary plexus (ICP) and deep capillary plexus (DCP).

As stated above, an advantage of OCTA/OCT over dye-based angiography (e.g., fluorescein angiography or indo-cyanine green angiography) is the non-invasive nature of OCTA/OCT imaging. Another key advantage of OCTA over dye-based angiography is its ability to visualize discrete capillary plexuses. Indeed, current commercially available OCTA devices can resolve three major capillary plexuses.

Figure 1:
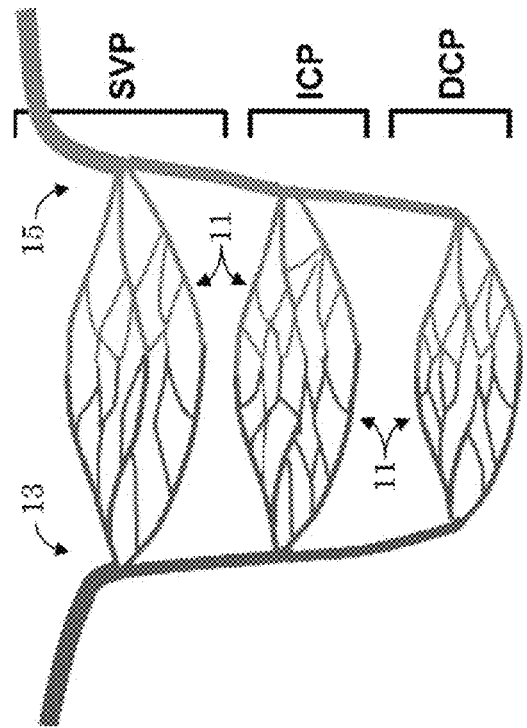
FIG. 1 provides a simplified view of three major capillary plexuses in three interconnecting layers; the superficial vascular plexus (SVP), the intermediate capillary plexus (ICP), and the deep capillary plexus (DCP).

FIG. 1 provides a simplified view of three major capillary plexuses in three interconnecting layers; the superficial vascular plexus (SVP), the intermediate capillary plexus (ICP), and the deep capillary plexus (DCP). Capillaries 11 are fine branching blood vessels that form a network structure (e.g., a plexus) between arteries and veins. FIG. 1 highlights the anatomical relationships between arterial 13 (shown in red) and a venous 15 (shown in blue) systems in the three vascular plexuses and the interconnecting layers.

Retinal vein occlusion (RVO) is a blockage of the small veins that carry blood away from the retina. RVO can result in the formation of collateral blood vessels, which are small capillary-like vascular branches that form in response to an obstruction in blood flow to bypass the obstruction and restore blood flow. By studying the retinal collaterals formed after the occurrence of retinal vein occlusion, Applicants have noted that all collateral vessels coursed through the DCP, while no collaterals were localized exclusively to the SVP, suggesting that the venous outflow predominantly originates in the ICP and DCP.

Figure 2:
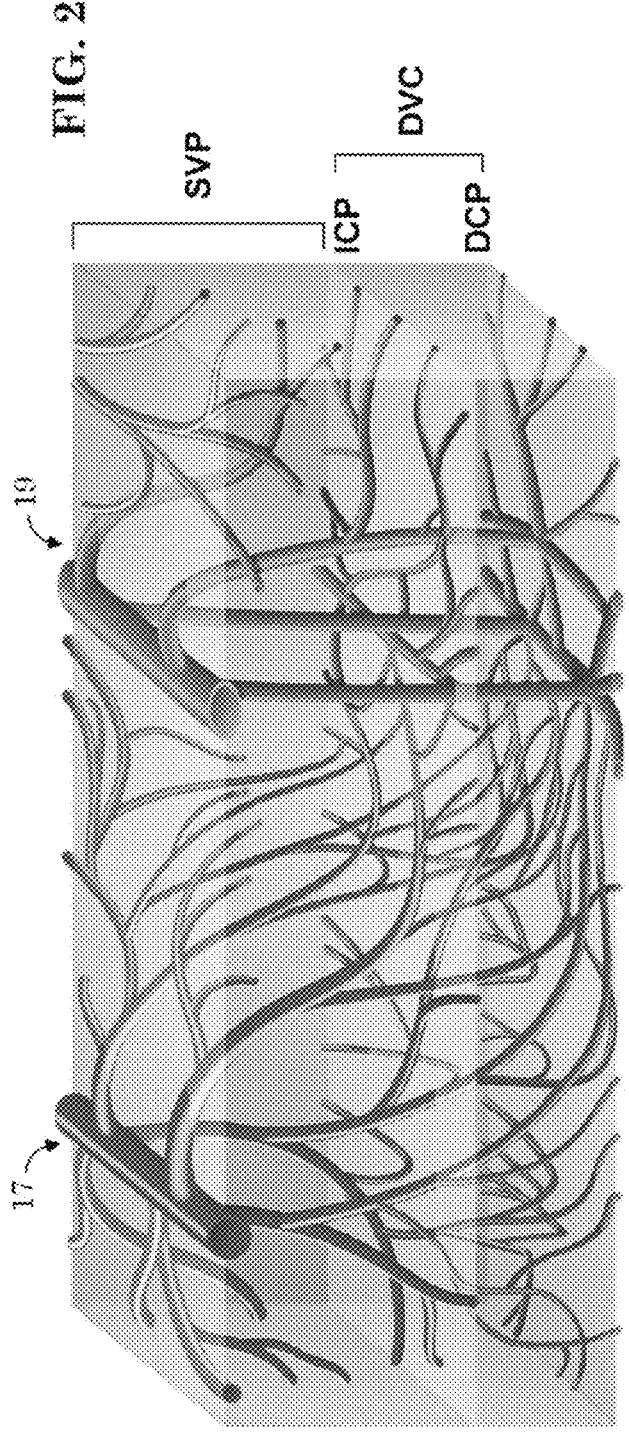
FIG. 2 is a schematic representation of a retinal vascular structure and blood flow with a predominantly series arrangement, particularly on the venous end.
Figure 3B:
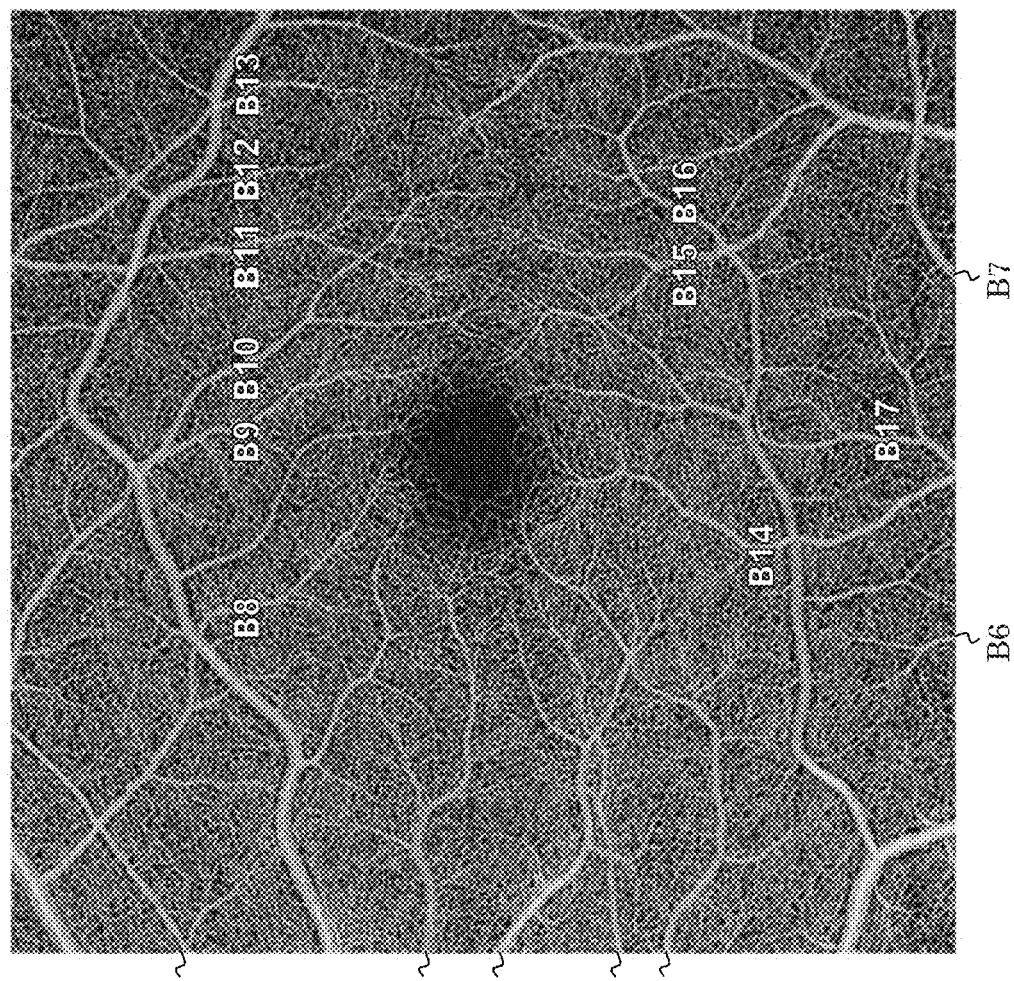
Figure 3A:

FIG. 2 is a schematic representation of an exemplary retinal vascular structure and blood flow with a predominantly series arrangement, particularly on the venous end. Several retinal layers are labeled for reference, including: the nerve fiber layer (NFL), ganglion cell layer (GCL), inner plexiform layer (IPL), inner nuclear layer (INL), and outer plexiform layer (OPL). The present example shows a more radiating pattern 17 (shown in red) in the superficial vascular plexus (SVP) specialized for arterial inflow with arterioles supplying all three capillary beds. It is also observed that local regions of vascular (e.g., capillary) convergence may characteristically form a more vortex-oriented pattern in the deep vascular complex (DVC), which may include the intermediate capillary plexus (ICP) and deep capillary plexus (DCP). This characteristic (e.g., featured) vortex arrangement of capillaries are specialized for venous outflow 19 (shown in blue). Note that all venous outflow courses through the DVC, which may be due to minimal arteriovenous communication in the SVP.

Applicants put forth that the featured vortices (and/or vascular convergence) arrangement of capillaries in the DCP may serve as a potential anatomic biomarker of venous origin. A study was conducted to develop an easy and reliable OCTA (or OCT) based method for an immediate visual classification of retinal vessels by recognizing that all vortices within the DCP are connected to veins (not arteries) in the more superficial retinal layers.

Before discussing the study, it is noted that, with improvements in segmentation algorithms, OCTA-rendered capillary layers have successfully been anatomically correlated to histologic sections. Generally, histology is the (ex vivo) study of the microscopic structure of tissue. Histology has shown that a physiologic avascular area, termed a capillary-free zone, is evident adjacent to retinal arteries. This capillary-free zone is also evident in OCTA images; however, histology correctly localized this finding to the SVP whereas OCTA may erroneously include portions of these more superficial vessels in the deeper layers. This capillary-free zone may also be used to differentiate arteries from veins in OCT-based images.

The conducted study followed the tenets of the Declaration of Helsinki, complied with the Health Insurance Portability and Accountability Act of 1996, and was approved by Western Institutional Review Board (Olympia, WA). Written informed consent was obtained from all subjects. Participants enrolled in this study were recruited from volunteers who agreed to undergo the examinations.

Retinal imaging for use in testing and training was acquired from normal eyes of healthy participants. Inclusion criteria were:
  (i) best-corrected visual acuity (BCVA)≥20/20;
  (ii) intraocular pressure (TOP)≤21 mmHg, and
  (iii) a spherical equivalent refractive error between −3 diopters (D) and +1 D. Exclusion criteria were:
  (i) history of any form of vitreoretinal diseases, high myopia, uveitis, glaucoma, or optic neuropathy;
  (ii) media opacities that might prevent successful imaging;
  (iii) prior intraocular surgery, laser treatment, or ocular trauma;
  (iv) systemic or neurological diseases that could affect retinal health, including diabetes, hypertension, dementia or multiple sclerosis.

Subjects underwent a complete ophthalmic evaluation including manifest refraction, uncorrected and best-corrected visual acuity (BCVA), intraocular pressure (TOP) measurement, slit lamp biomicroscopy examination, ophthalmoscopic examination, high-resolution true color confocal color fundus photography (EIDON®, CenterVue®, Padua, Italy), and swept source (SS)-OCTA (PLEX Elite® 9000; Carl Zeiss Meditec®, Inc, Dublin, CA, USA). Scan patterns acquired on the SS-OCTA device were the default 3×3 mm and 6×6 mm OCTA cube scans.

It is to be understood that similar training and testing image sets may be used to train/test both human medical practitioners (e.g., to determine if the present methods provide a benefit for clinical training of personnel) and machine learning models. Additionally, computer algorithms may also be created based on the present methods for differentiating arteries and veins in ophthalmic images. For ease of discussion, the training and testing of human medical practitioners is discussed first, and a discussion of machine learning models and algorithms follows.

Figure 4B:
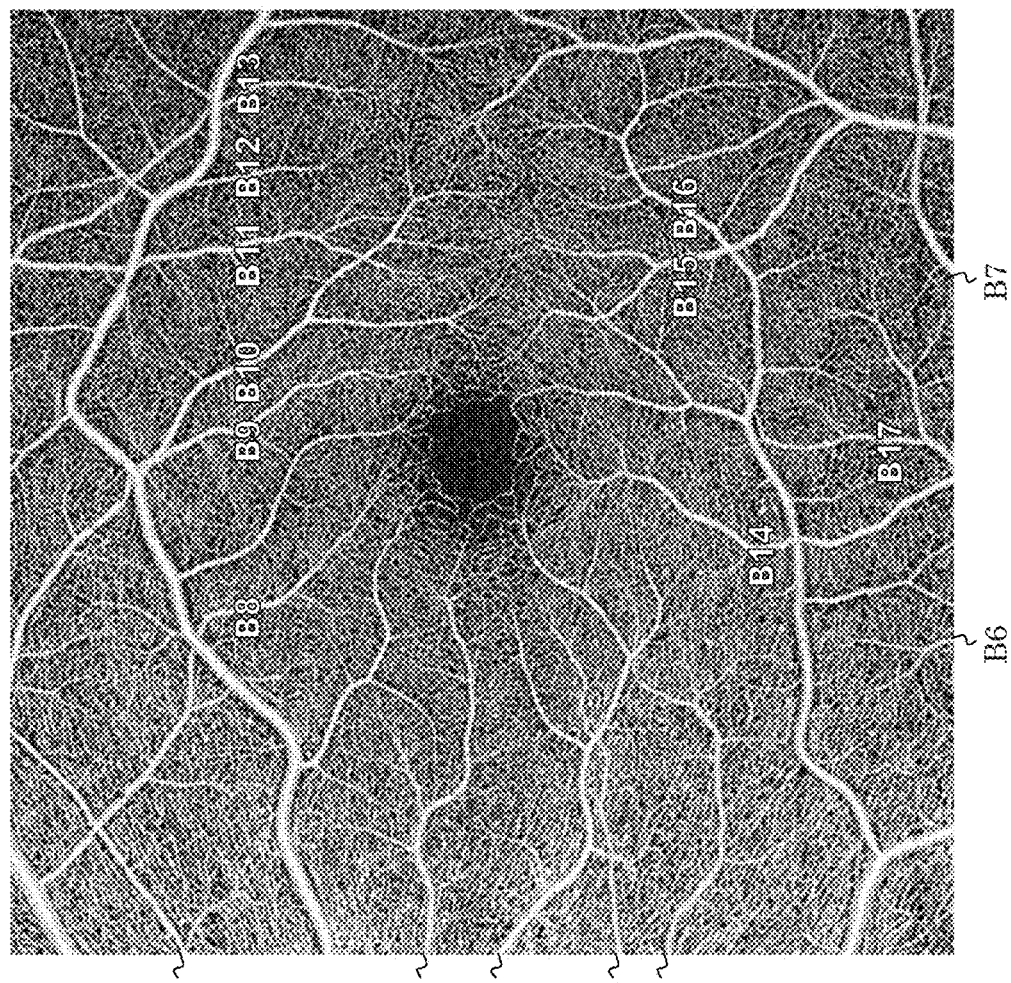
Figure 4A:
Figure 5B:
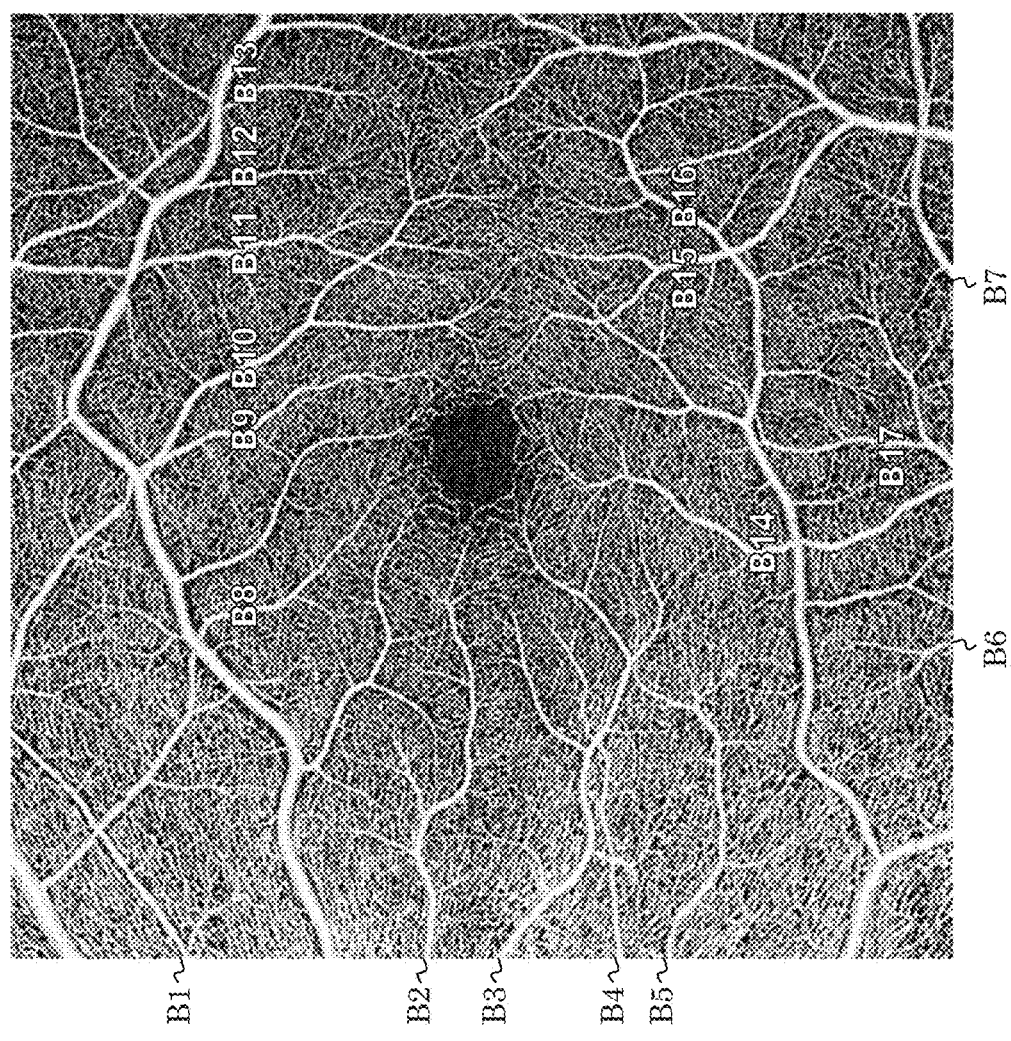
Figure 5A:
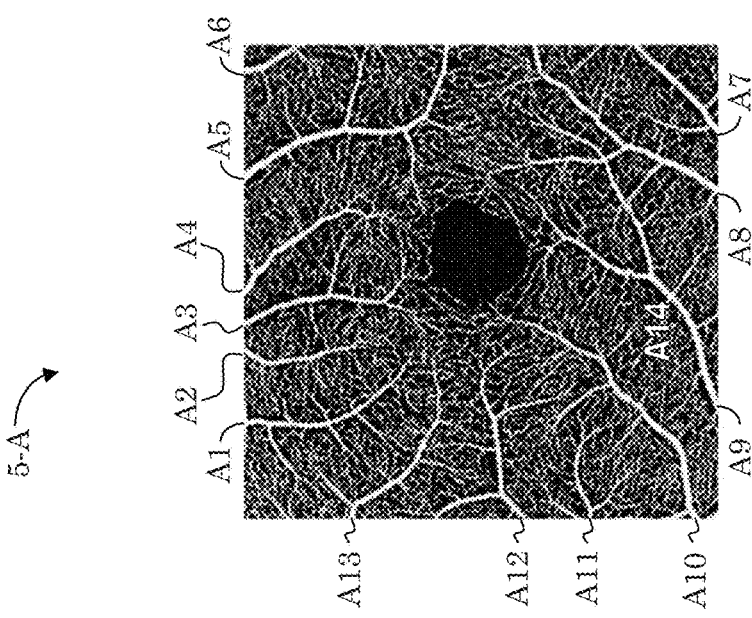

Training and Grading:

Nine 3×3 mm and nine 6×6 mm OCTA scan volumes centered on the fovea from 18 eyes of 14 healthy subjects (8 males and 6 females; 39.8±17.1 years of age, range 15-71 years) were used to create training and testing image sets for use in this study. A total of 147 vessels from the 9 3×3 mm image sets and 193 vessels from the 9 6×6 mm image sets were labeled with numbers for later assignment as artery or vein by study participants. Image sets for training and testing were created by exporting the automatically segmented default en face slabs (color retina depth-encoded, greyscale full-thickness retina, SVP, and DCP with projection removal) from each OCTA volume and pasting them into a PowerPoint (Microsoft® Corporation, WA, USA) file, one slab per slide. Blood vessels were labeled with numbers in each slide. High-resolution color fundus photographs were used for identification of arteries and veins based on the following characteristics: arteries are brighter in color than veins; arteries are thinner than neighboring veins; the central light reflex is wider in arteries and smaller in veins; and arteries and veins usually alternate around the optic disk before branching out Multiple training/testing sets may be created for training/testing of human technicians and/or machine learning models. Each training/testing set may include multiple image sets of normal eyes (e.g., the same eye). Alternatively, training sets of diseased eyes may also be used for training/testing purposes. FIGS. 3A-6A, along with corresponding FIGS. 3B-6B, illustrate multiple image sets that together may constitute part (or the whole) of a training/testing set. In the present example, each of FIGS. 3A/3B, 4A/4B, 5A/5B, and 6A/6B provides an optical coherence tomography angiography (OCTA) image set. It is to be understood that a training/testing set my also include (or consist of) OCT (structural) images. In the present example, each image set includes a 3×3 mm image (e.g., images 3-A to 6-A in FIGS. 3A to 6A, respectively) and a corresponding 6×6 mm image (e.g., images 3-B to 6-B in FIGS. 3B to 6B, respectively). Vessels that need to be classified as arteries or veins are numbered on each image, or slab. For example, vessels in images 3-A to 6-A that are to be classified are labeled A1 to A14, and vessels in images 3-B to 6-B that are to be classified are labeled B1 to B17. Each image set of FIGS. 3A/3B, 4A/4B, 5A/5B, and 6A/6B provides a different imaging modality. The image set of FIGS. 3A and 3B consists of color retina depth-encoded images 3-A and 3-B. FIGS. 4A and 4B provide greyscale full-thickness retina images 4-A and 4-B. FIGS. 5A and 5B provide superficial plexus images 5-A and 5-B, and FIGS. 6A and 6B show deep plexus images 6-A and 6-B (optionally with projection removal).

Figure 7A:
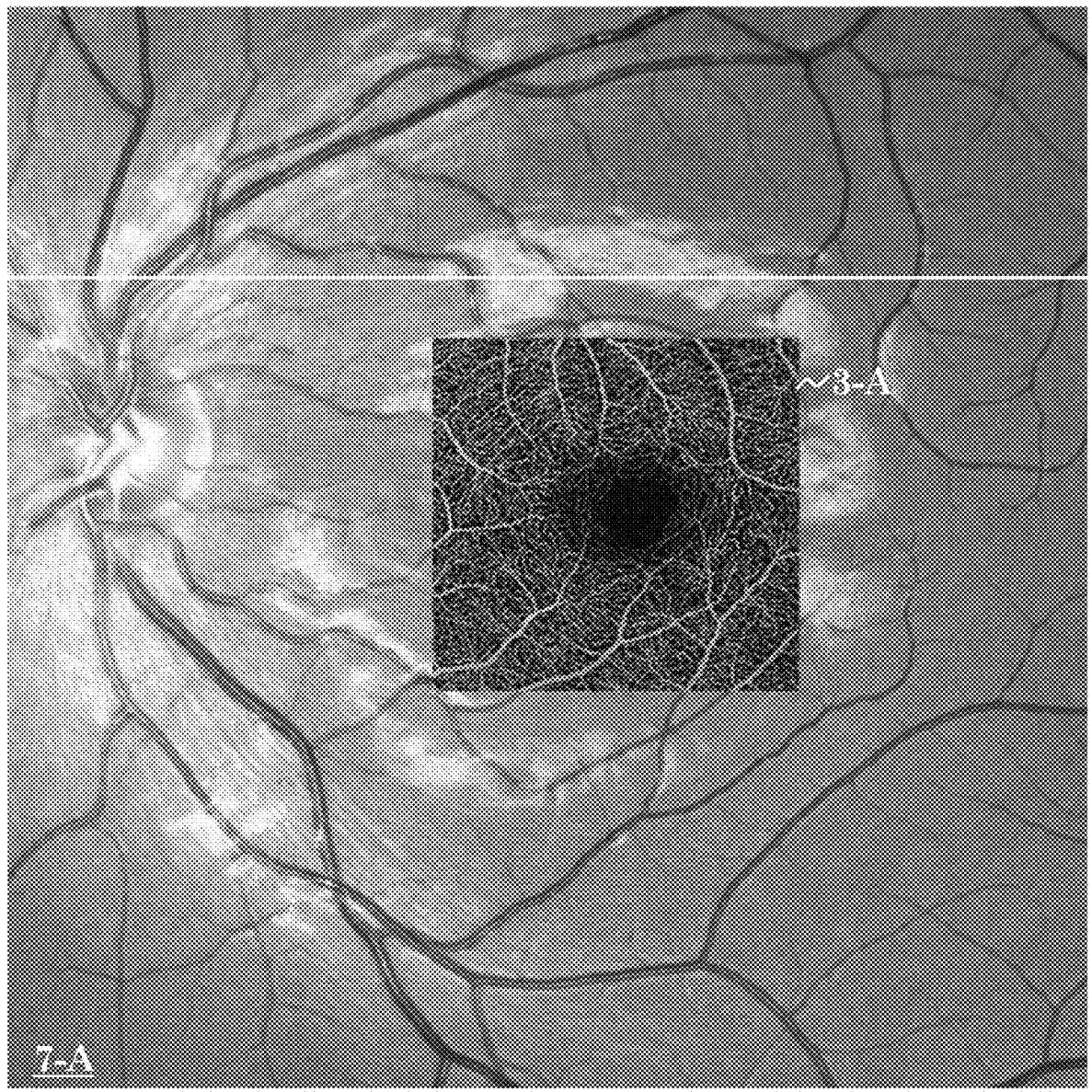
FIG. 7A shows the 3×3 mm, color depth-encoded OCTA image of FIG. 3A aligned to a corresponding high-resolution color fundus photograph.
Figure 7B:
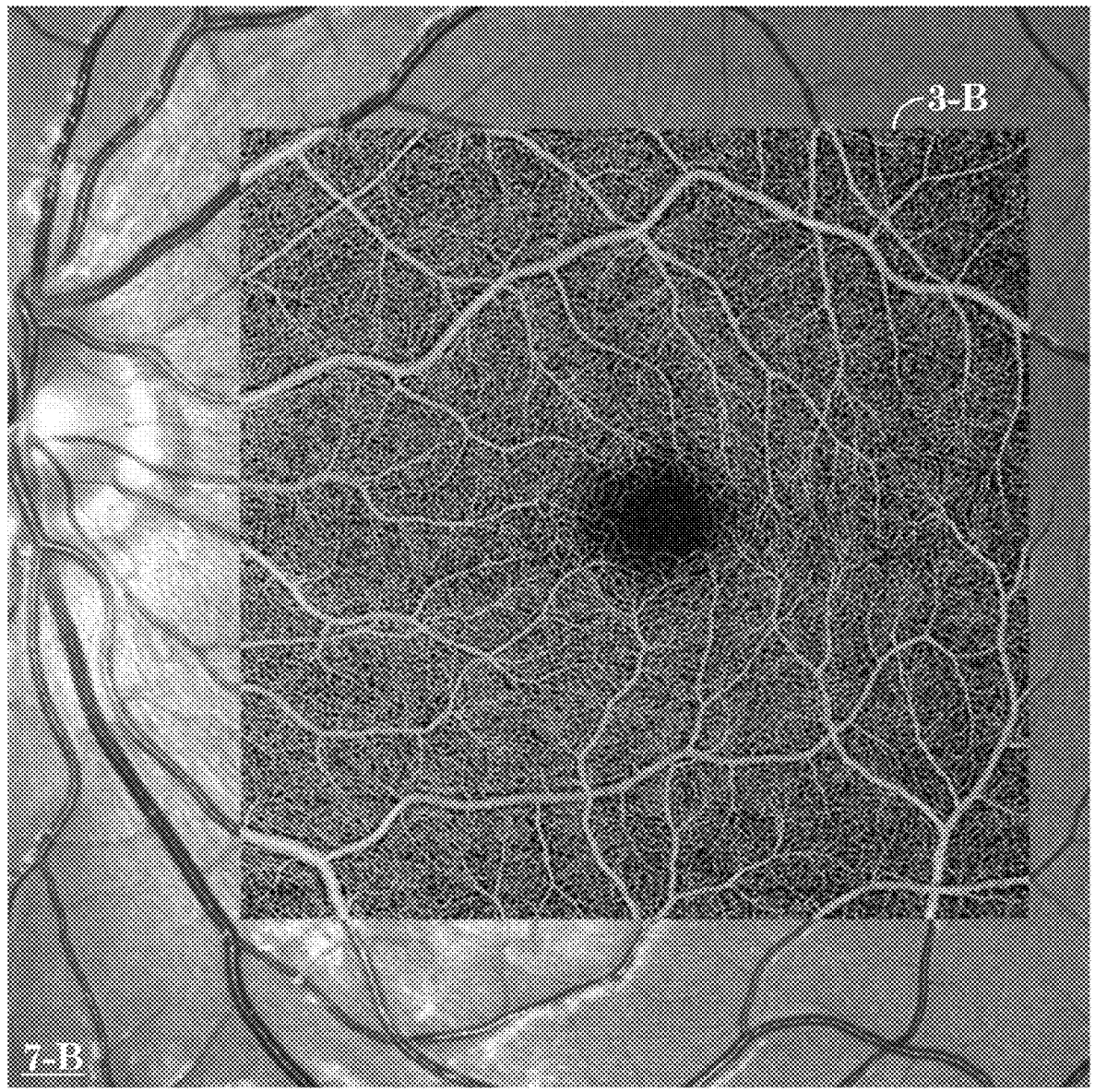
FIG. 7B shows the 6×6 mm, color depth-encoded OCTA image of FIG. 3B aligned to a corresponding high-resolution color fundus photograph.

When preparing these image sets, ground truth artery and vein designations may be obtained by use of high-resolution color fundus photographs, and identifying the artery and veins in the color fundus photographs using techniques well-known in the art. For instance, arteries may be distinguished from veins in high-resolution color fundus photographs by size, shape, vessel crossing patterns, color, brightness, optical reflexes, etc. The artery and vein designations obtained from the color fundus photographs may then be transferred to corresponding image sets to define their ground truth artery/vein designations. For example, FIG. 7A shows the 3×3 mm, color depth-encoded OCTA images 3-A (of FIG. 3A) aligned to a corresponding (optionally large FOV) high-resolution color fundus photograph 7-A, such as by use of retinal vessels as landmarks. Artery and vein designations from high-resolution color fundus photograph 7-A may be correlated to vascular structures in color depth-encoded OCTA images 3-A. Similarly, FIG. 7B shows the 6×6 mm, color depth-encoded OCTA images 3-B (of FIG. 3B) aligned to its corresponding (optionally large FOV) high-resolution color fundus photograph 7-B. Optionally, the artery/vein designation of the vasculature of images 4-A to 6-A may be identified by correlation to the identified vasculature of image 3-A, and the artery/vein designation of vasculature of images 4-B to 6-B may be correlated to that of image 3-B. In this manner, the high-resolution color fundus photographs 7-A and 7-B may be used to confirm the identity of each numbered vessel as either artery or vein.

A sample training/testing of human technicians included nine ophthalmologists without previous OCTA experience from 2 institutions (5 from Bascom Palmer Eye Institute, University of Miami Miller School of Medicine, Miami, Florida and 4 from Zhongshan Ophthalmic Center, Sun Yat-sen University, Guangzhou, China). To help identify which criteria is most useful for classifying arteries and veins, the nine ophthalmologists were tested in 3 stages, with each stage providing additional criteria for differentiating arteries from veins. In each stage, the ophthalmologists (or "graders") were instructed to classify all labeled vessels (e.g. enumerated vessels as discussed above) in sample training/testing sets as arteries or veins. In stage 1, no training (or specific criteria) was provided such that untrained classification based on graders' own assessment was performed.

Figure 8:
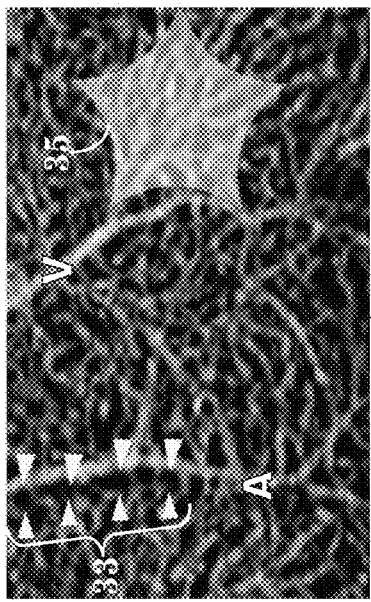
FIG. 8 provides a close-up view of an en face, color depth-encoded image highlighting some artery/vein classification criteria suitable for OCT-based images.

FIG. 8 provides a close-up view of an en face, color depth-encoded image 31 highlighting some artery/vein classification criteria suitable for OCT-based images. It is to be understood that the identification criteria discussed herein may be applied to other OCT-based images, such as B-scan, A-scan, and C-scans. Prior to stage 2, graders were taught that a capillary-free zone 33 (highlighted by white arrowheads) is an anatomic feature of arteries. Prior to stage 3, graders were further trained to identify veins by their origin in vortices within the deep capillary plexus, DCP, (highlighted by curved pentagons 35) and which may be characterized as a (e.g., green) convergence of capillaries in the present color depth-encoded image/slab 31, and to consider that arteries ("A") and veins ("V") typically alternate as each vein drains capillary beds perfused by adjacent arteries in stage 3. In this manner, the most useful criteria for differentiating arteries from veins in OCT-based images may be identified, and these identified criteria may be used to create machine algorithms and/or to train machine learning models effective for identifying arteries and/or veins in OCT-based imaged.

The training time prior to stage 2 and stage 3 was no more than 15 minutes. During training, each participant was asked to demonstrate an understanding of the technique by correctly identifying the vascular features on images from an image set they had previously graded. Three 3×3 mm and three 6×6 mm scans were randomly chosen and used in each stage. Data including grading performances and the average grading time spent on each vessel in each stage regardless of the scanning patterns of the images used for grading were de-identified and recorded in a Microsoft® Excel® 2016 database (Microsoft® Corp., Redmond, WA, USA).

Figure 9F:
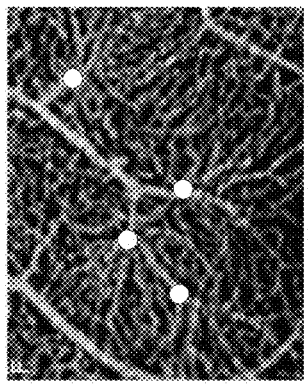
FIG. 9F provides an expanded view of the white dotted box of FIG. 9A, highlighting the centers of convergence of capillaries (such as defined by vortices), which are indicative of veins.
Figure 9E:
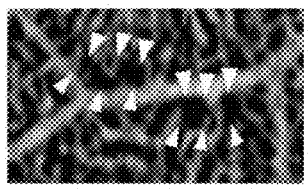
FIG. 9E provides an expanded view of the solid white line box of FIG. 9A, highlighting capillary-free zones, which are indicative of arteries.
Figure 9A:
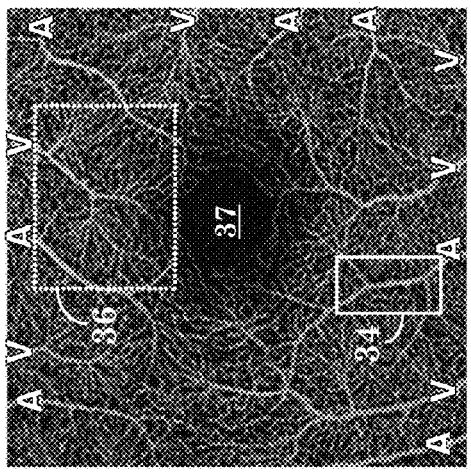
FIGS. 9A to 9C provide an example set of 3×3 mm optical coherence tomography angiography images centered on the fovea and with labeled arteries and veins.
Figure 9D:
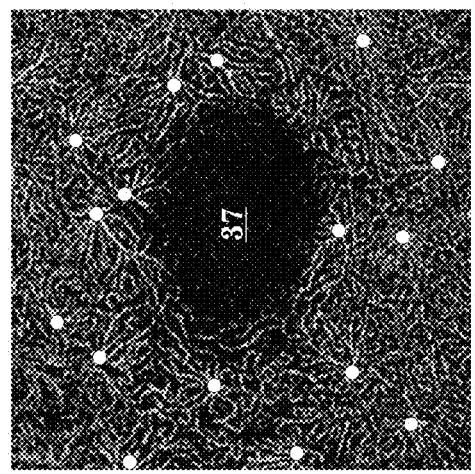
FIG. 9D shows vortices marked with white dots indicating the centers of capillaries convergences on a deep capillary plexus (DCP) image.
Figure 9C:
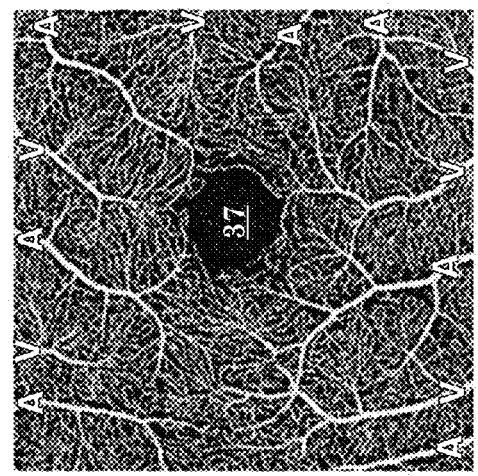
Figure 9B:
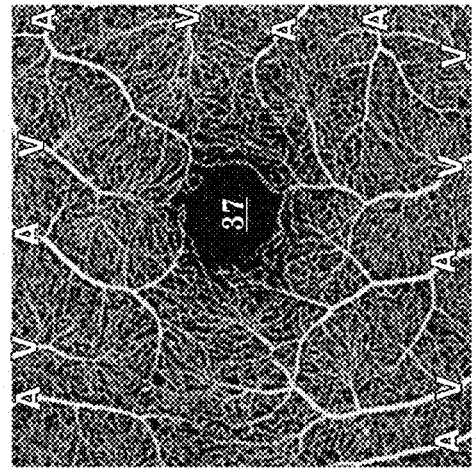
Figure 10B:
FIGS. 10A and 10B show high-resolution color fundus photographs, centered on the fovea, and corresponding to the OCT scans of FIGS. 9A to 9C.
Figure 10A:
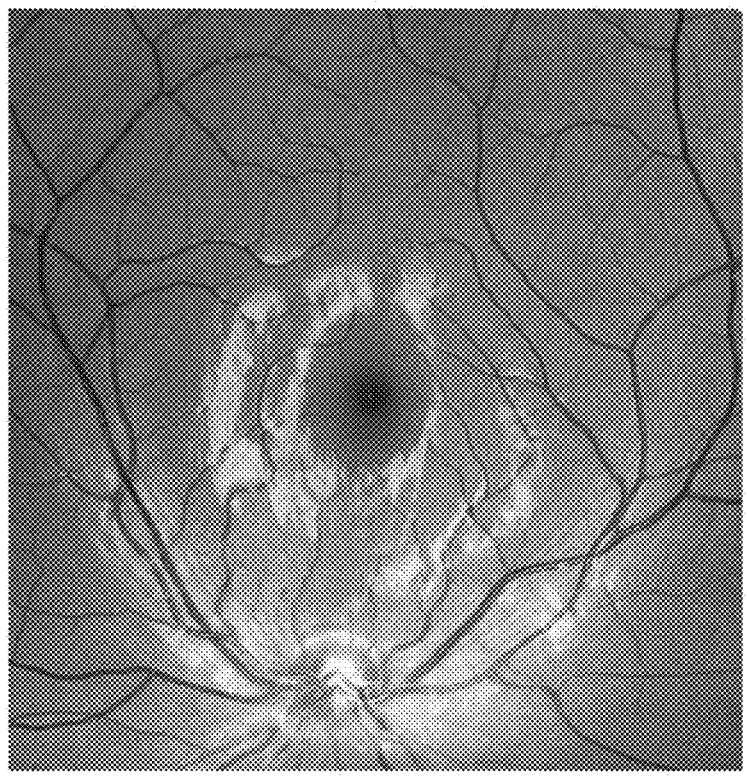

FIGS. 9A to 9C provide an example set of 3×3 mm optical coherence tomography angiography (OCTA) images centered on the fovea 37 and with labeled arteries ("A") and veins ("V"). FIG. 9A shows arteries (A) and veins (V) classified and labeled on a retina, color depth-encoded image. FIG. 9B shows arteries (A) and veins (V) labeled on a greyscale full-thickness retina image, and FIG. 9C shows the labeling of arteries (A) and veins (V) on a superficial plexus slab. For illustration purposes, FIG. 9D shows vortices marked with white dots indicating the centers of capillaries convergences on a deep capillary plexus (DCP) image (optionally with projection removal). These vortices may, for example, be automatically identified by use of a computer algorithm or trained machine model, or a technician may be trained to identify vortices in the DCP. The vessels of FIGS. 9A-9C were classified based on the following criteria: superficial arteries have adjacent capillary-free zones (e.g., white arrowheads 33 in FIG. 8), and the vortices 35 in the DCP drain into (e.g., are coupled/connected to) veins. For example, FIG. 9E provides an expanded view of the solid white line box 34 of FIG. 9A, and arrowheads highlight adjacent gaps free of capillaries (capillary-free zones), which are indicative of arteries. Similarly, FIG. 9F provides an expanded view of white dotted box 36 of FIG. 9A, and white dots highlight the centers of convergence of capillaries, which are indicative of veins. The classifications were confirmed (as described above) using artery/vein designations from a corresponding high-resolution color fundus photograph, shown in FIG. 10A (and its enlargement shown in FIG. 10B) centered on the fovea with a size of 3×3 mm.

Statistical Analysis:

Descriptive results were presented as mean±standard deviation (SD) with range (minimum, maximum). The Kolmogorov-Smirov test and the Levene test were conducted to test the normality and homogeneity of variance, respectively. The correlation between accuracy and grading time and between accuracy and a grader's years of practicing ophthalmology were analyzed using Pearson correlation coefficient. The accuracy between different grading stages and the accuracy between the two scanning patterns in each grading stage were compared using generalized estimating equations (GEE). Statistical analysis was conducted using SPSS version 22.0 (SPSS Inc, Chicago, Illinois, USA) and a P value of <0.05 was considered statistically significant.

Results

FIG. 11 provides Table 1, which summarizes the overall grading accuracy and the separate accuracies for the 3×3 mm and 6×6 mm image sets at each stage. The average time spent on each vessel was (16.5±5.4) seconds(s), (8.5±3.6) s, and (15.6±8.1) s in stages 1, 2, and 3, respectively. The average years in practice for 9 ophthalmologists was (6.4±4.2) years. FIG. 12 provides Table 2, which displays the sensitivity and specificity for identifying retinal veins at each stage. FIG. 13A provides Table 3, which displays the correlation between grading accuracy and mean time spent on each vessel during each stage. FIG. 13B provides Table 4, which displays the correlations between grading accuracy at each stage and graders' mean years in practice subdivided by scan pattern size.

Using the present training method/system, grading accuracy increased from 50.4% in stage 1, to 75.4% in stage 2, and to 94.7% in stage 3. In post-assignment interviews, graders expressed great difficulty grading vessels in stage 1 as the OCTA images lack visual cues, such as color, contrast, width, and shape, which they would typically use to distinguish arteries from veins when evaluating other forms of retinal imaging modalities, such as color fundus images. In addition, graders could not trace vascular structures to the optic nerve since neither scan pattern includes the optic disc when it is centered on the fovea. That is, OCT-based images typically have a much smaller FOV than fundus images, and often lack major structural features of the retina, such as the optic disc, that may be used as a reference.

In stage 2, graders used information from histologic studies of human retinas demonstrating the presence of capillary-free zone present around retinal arteries, such as may develop during embryogenesis. These areas may exist where transmural oxygen diffuses to satisfy the metabolic demands of cells immediately adjacent to oxygen rich superficial retinal arteries. Grading performance in stage 2 indicated that awareness of the periarterial capillary-free zone could improve accuracy to 75.4%. However, graders had difficulty applying this technique to smaller arteries for which the presence or absence of a capillary-free zone was difficult to discern, and when they tried to follow the course of the larger arteries distal to arteriovenous crossings.

In stage 3, graders were taught to identify veins by their origin in the vortices within the DCP, which they were then able to trace back to arteriovenous crossings. When graders had separate complimentary strategies for identifying arteries and veins, grading accuracy increased to 94.7%. Use of vortices (e.g., a vascular convergence) within the DCP provided a local reference within the (typically small) FOV of the OCT-based image to identify veins without the need for more established retinal landmarks, such as the optic disc, which may not be visible within the OCT-based image.

Figure 14:
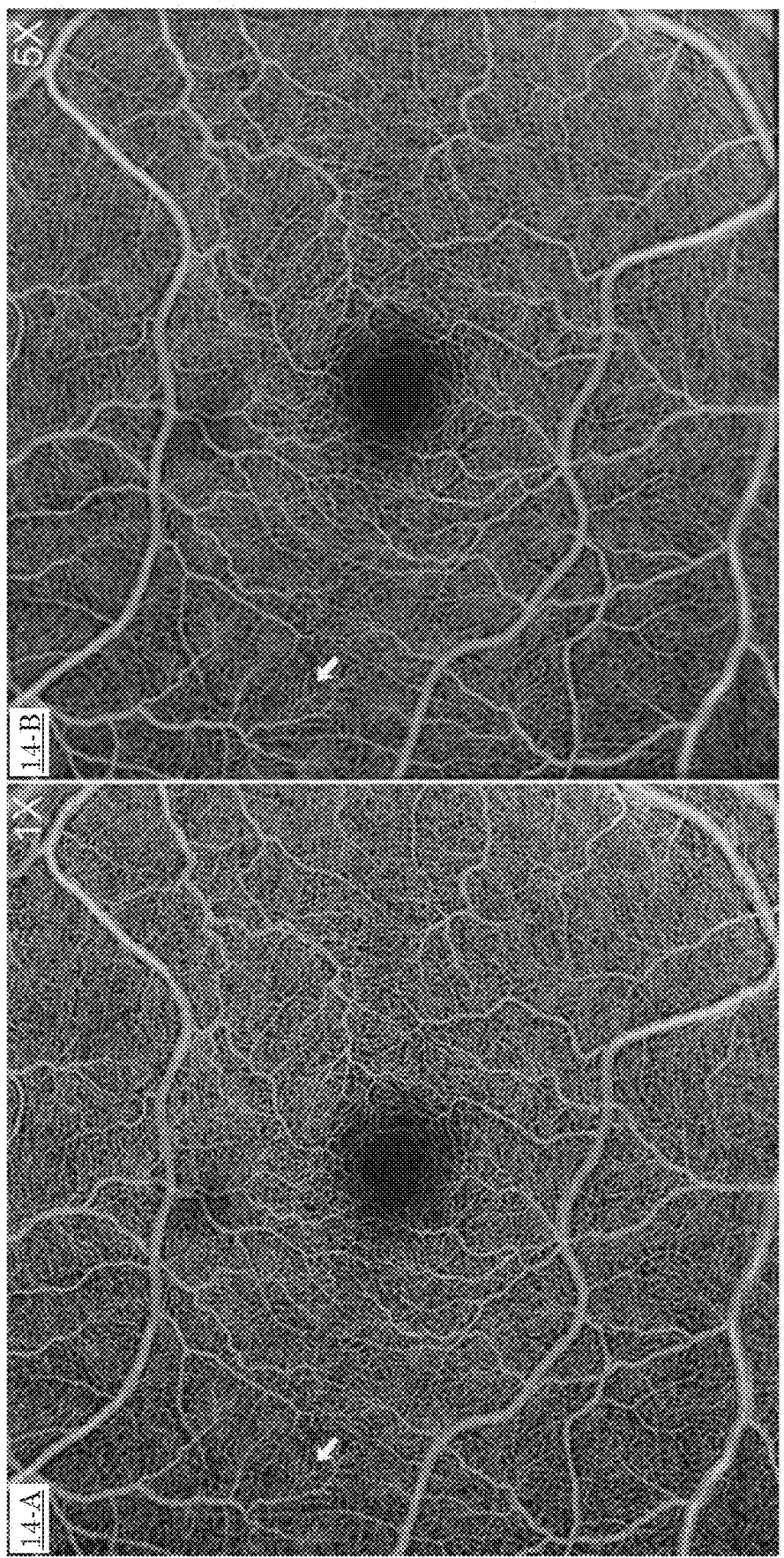
FIG. 14 illustrates a single 6×6 mm image 14-A and an averaged image 14-B constructed from averaging the single 6×6 mm image 14-A with four additional 6×6 mm images of the same region.

In stage 2 and 3, grading accuracy for 3×3 mm scans was significantly higher than for 6×6 mm scans. This may be due to the different A-scan densities used in their 2 grid patterns. The 3×3 mm images in the present study used 10 μm spacing between A-scans in their scan pattern, while the 6×6 mm images used 12 μm spacing in their scan pattern. Also in the present study, the 3×3 scan pattern used 4× averaging for each B-scan, while the 6×6 mm scan pattern used only 2× averaging for each B-scan. Therefore, both the periarterial capillary-free zone and the DCP vortices were more easily recognizable in the smaller, higher resolution, and less noisy 3×3 images. Also, since all studies were centered on the fovea, vessels at the superior, inferior, and temporal margins of 6×6 mm scans were often smaller than those on 3×3 mm scans, making it more difficult to recognize these important scan features. One technique for enhancing vascular detail in 6×6 mm and larger scan patterns may be to average multiple tracked scan acquisitions, such as illustrated in FIG. 14. More specifically, FIG. 14 illustrates a single 6×6 mm image 14-A and an averaged image 14-B constructed from averaging image 14-A with four additional 6×6 mm images of the same region. White arrows illustrate the difference in image quality between the single 6×6 mm image of 14-A and the five 6×6 mm images registered and averaged together to define the less noisy image 14-B.

In the present study, graders uniformly reported that among the four slabs provided in each image set (e.g., slabs as illustrated in FIGS. 3 to 6), the color depth-encoded slab (e.g., 3A and/or 3B) was the most useful in all aspects of grading. Color coding of the superficial and deep vessels made identifying the connection of veins to the deep capillary vortices simply a matter of identifying the convergence of thin green linear structures (e.g., green identifies the DCP). After completing the training exercises, most graders expressed that this single visualization would be sufficient for grading. In fact, graders in stage 3 relied primarily on the retinal, color depth-encoded image for artery/vein classification and typically ignored the three additional slabs, as they seemed to provide no (or little) additional distinguishing information.

Interestingly, grading accuracy was not statically correlated with grading time or graders' years in practice. For all participants, training grading sessions were completed in under 15 minutes. These results suggest that the vessel classification method described herein may be used to train non-ophthalmologist, including technician graders in imaging reading centers.

Figure 15:
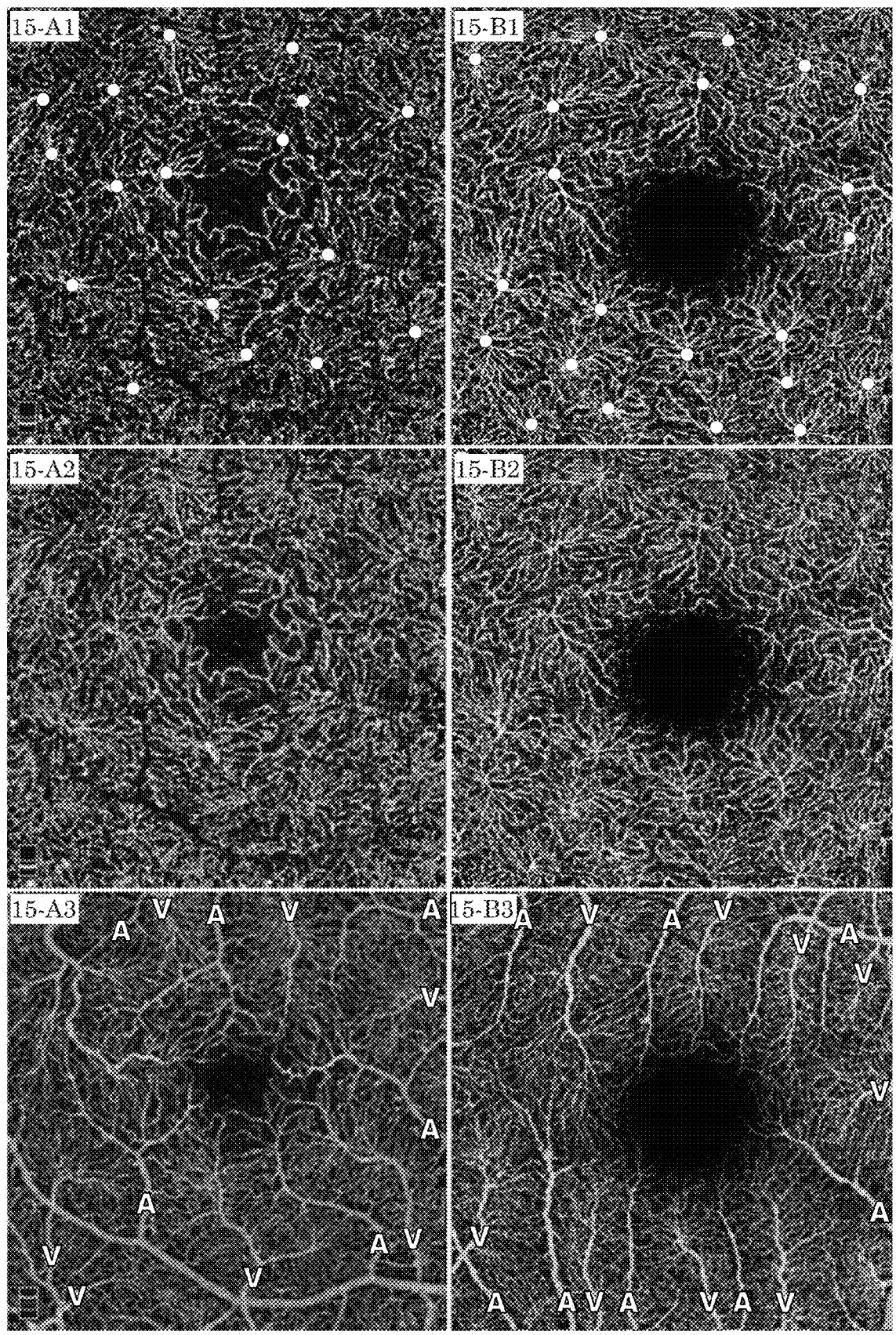
FIG. 15 illustrates two sets of example images (15-A1 to 15-A3 and 15-B1 to 15-B3) suitable for the present invention and acquired using commercially available OCTA systems.

It is noted that a color depth-encoded image suitable for the present invention may be constructed from other standard acquisition OCT/OCTA methods. For example, a suitable depth-encoded image may be defined by separately obtaining a superficial and deep slab/image and combining the two, such as by use of image processing. For example, a suitable image may be obtained by color coding a superficial slab or a deep slab and combining both into a composite image using image processing tools, such as ImageJ (a publicly available Java-based image processing and analysis tool available from the U. S. National Institutes of Health, Bethesda, Maryland, USA, and accessible from website "imagej.nih.gov/ij/") or Adobe® Photoshop® (image processing software available from Adobe Inc., CA). FIG. 15 provides examples of identifying arteries and veins on standard acquisitions performed on two commercially available optical coherence tomography angiography (OCTA) instruments. The left-column images (15-A1 to 15-A3) are from an RTVue XR Avanti system (Optovue, Inc, Fremont, CA, USA), and the right-hand column images (15-B1 to 15B-3) are from a Heidelberg Spectralis OCT2 system (Heidelberg Engineering, Heidelberg, Germany). In images 15-A1 and 15-B1, the centers of vortices are marked with white dots on the deep capillary plexus (DCP) slab with projection removal. In images 15-A2 and 15-B2, the vortices are then color-coded with green on the DCP slab. In images 15-A3 and 15-B3, a combination of the color-coded deep slab with a translucent grey-scale superficial slab enable distinction between arteries (A) and veins (V).

Figure 16:
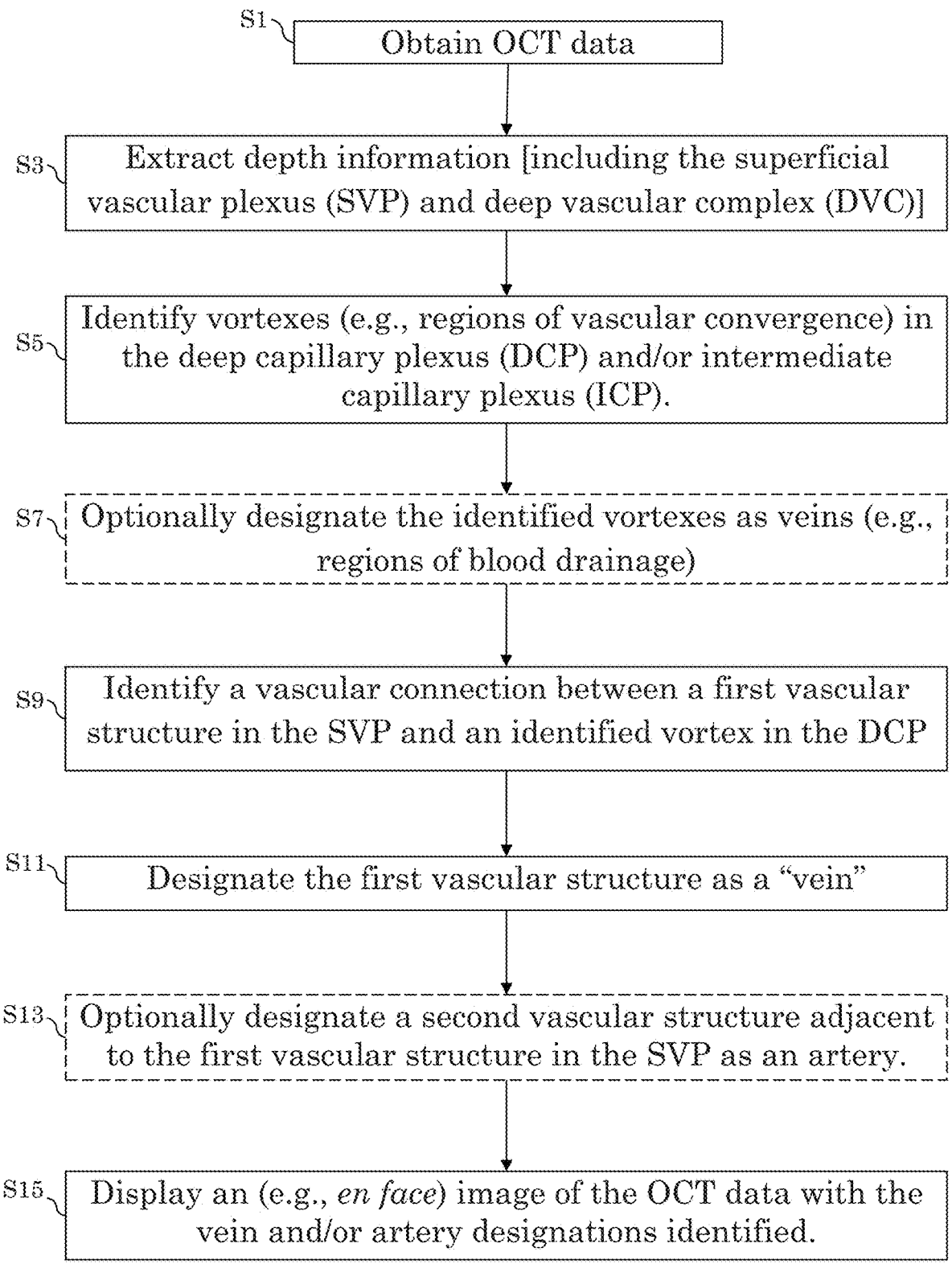
FIG. 16 is a flow chart illustrating an exemplary method of implementing the present invention.

The present methods can also be applied to automatic vessel classification using specialized algorithms and/or machine learning techniques and/or artificial intelligence. FIG. 16 illustrates an exemplary method of implementing the present invention. The present example begins by obtaining OCT data (step S1), which may be OCTA vascular flow data and/or OCT structural data, and may be A-scans, B-scans, C-scans, en face images of selected tissue slabs, etc. The present invention may be applied to any, or a combination, of different OCT data scans. For example, the present invention may be applied to B-scans or volume scans (e.g., C-scans) by identifying different plexuses at different depths in the OCT data. For ease of discussion, and to maintain continuity with the above-provided examples, the present discussion provides color, depth-encoded, en face images of the retina, but it is to be understood that the present methods (e.g., specialized algorithms and/or machine learning methods) may be implemented using different types of OCT data, such as OCT/OCTA B-scans, volumes, etc.

In step S3, depth information is extracted from the obtained OCT data. More specifically, vascular beds at different depths are identified. For example, the superficial vascular plexus (SVP) and a deeper plexus are extracted. The deeper plexus may be extracted from the deep vascular complex (DVC), e.g., the intermediate capillary plexus (ICP) and/or the deep capillary plexus (DCP). Various methods of identifying vessels are known. For example, vessels in OCT data may be detected by intensity analysis between different retinal layers. In the present example, the deep capillary plexus (DCP) is extracted and analyzed, but the present method may alternatively, or in combination, be applied to other deep plexuses, such as the intermediate capillary plexus. This may be the case, for example, when dealing with a diseased eye, which develop plexus-growth at atypical depths.

Assuming that the SVP and DCP are extracted in step S3, the DCP is analyzed to identify regions of vascular convergence (or vortices) in step S5. This may include multiple image processing steps, such as image segmentation to extract vascular structures. For example, the DCP data/image (or the entire color, depth-encoded, en face slab) may be binarized and a skeleton algorithm and/or edge detection may then be applied to the binarized data. As is explained above, the DCP may be identified by use of depth information. However, the DCP may also be differentiated from vascular structures in the SVP (for example, if depth information is missing) by use of the edge information, which may be used to determine the diameter of a vessel. Generally, vascular structures in the DCP are much thinner than the vascular structures in the SVP. The resultant skeleton and/or edge information may be analyzed, such as by the use of a moving window, to identify vortex structures (or regions of vascular convergence, or concentrations, of vessel structures, or vessel structure have a generally vortex formation) in the DCP (or ICP). For example, vessel concentration may be determined by a density measure of vascular structures within a window, such as by obtaining a ratio of a vascular pixel count to a non-vascular pixel count. Alternatively, or in combination, a vector field representation of the vasculature within the DCP may be defined. Regions of vascular convergence (e.g. vortices) may then be determined from the vector field. For example, a heat map of vascular concentration may be generated from the vector field, which may identify vortices by color on a display. The vector field may be defined by applying a Hessian filter to the DCP to identify its vasculature. Generally, a Hessian filter may describe a local curvature by extracting eigen vectors from $2^{nd}$ order derivatives, and thereby determine direction. Alternatively, a 2D gradient may be applied to the DCP to define the vector field (or heat map) directly. Further alternatively, or in combination, the vortices may be identified by machine learning techniques. For example, a machine learning model (e.g., deep learning neural network, such as discussed below) may be trained to identify concentrations of vessel in the DCP. Alternatively, another type of machine learning model (e.g., a support vector machine) may be trained to identify these convergences/concentrations of vascular structures. A neural network may be trained using a training set of OCT-based images where the output training set includes OCT-based images with manually delineated vortices and/or manually delineated arteries and veins (such as identified from the use of corresponding color fundus images), and the input training set includes the same OCT-based images without the delineated vortices, arteries, and/or veins.

Optionally, the identified vortices (e.g., regions of vascular convergences) from step S5 may be designated as veins. As discussed above, the vortices may correspond to regions of blood drainage. Alternatively, or in addition, the identified vortices may optionally be superimposed on the obtained OCT data from step S1 and presented on an electronic display to a medical practitioner, which may then use the identified vortices to manually identify arteries and veins in the OCT data, as discussed above.

However, if it is desired for the present method/system to automatically identify veins and arteries in the OCT data, the process may proceed to step S9, which identifies vascular connections between "first vascular structure(s)" in the SVP and the identified vortices. This may be accomplished using traditional image processing steps, as discussed above, and/or may also include machine learning techniques, as discussed below. The identified first vascular structures in the SVP may be designated as veins (step S11).

Optionally, arteries may also be identified (step S13). As discussed, above, arteries and veins typically form an alternating pattern. Thus, a second vascular structure adjacent a first vascular structure may be designated an artery. Arteries may be identified, or verified, by the presence of a capillary-free zone adjoining the second vascular structure.

The obtained OCT data may then be presented to the medical practitioner (e.g. as an en face image, and preferably a color depth en-coded en face image) with the vein and/or artery designations identified (step S15), such as by color code or direct labeling. Alternatively, a technician may be presented with an image of the OCT data (e.g., on an electronic display) without labeling veins or arteries, and the technician may select one or more vascular structures within the displayed OCT data, such as by use of an electronic input device (e.g., touch screen, computer mouse, keyboard, etc.). The present system may respond by identifying (e.g., by color code or translucent label) the selected vascular structures as veins or arteries.

Machine Learning Applications

As discussed above, the present invention may be implemented, at least in part, by using machine learning techniques, such as by use of a support vector machine or by a (e.g., deep learning) neural network. Generally, a support vector machine (SVM) is a machine learning, linear model for classification and regression problems, and may be used to solve linear and non-linear problems. The idea of an SVM is to create a line or hyperplane that separates data into classes. More formally, an SVM defines one or more hyperplanes in a multi-dimensional space, where the hyperplanes are used for classification, regression, outlier detection, etc. Essentially, an SVM model is a representation of labeled training examples as points in multi-dimensional space, mapped so that the labeled training examples of different categories are divided by hyperplanes, which may be thought of as decision boundaries separating the different categories. When a new test input sample is submitted to the SVM model, the test input is mapped into the same space and a prediction is made regarding to what category it belongs based on which side of a decision boundary (hyperplane) the test input lies.

In an exemplary embodiment, an SVM may be used for identification of vortex structures in the DCP and/or for vein/artery designation in the SVM, ICP, and/or DCP. For example, an SVM may be trained to identify vortices in the DCP, and to identify vascular connections between the SVM, or ICP, and the identified vortices. Various SVM architectures known in the art, and the specific SVM architecture(s) used for this task is not critical to the invention. For example, a least squares SVM may be used for image classification. Both pixel-level features (e.g., color, intensity, etc.) and texture features may be used as inputs to the SVM. Optionally, an ensemble of SVMs, each providing specialized classification, may be linked to achieve better results.

The vortex identification of steps S5/S7 and/or the vein/artery designation steps of S9 to S13 may also be implemented by use of a neural network (NN), machine learning (LM) model. Various examples of neural networks are discussed below with reference to FIGS. 27 to 30, any, or a combination, of which may be used with the present invention.

Figure 17:
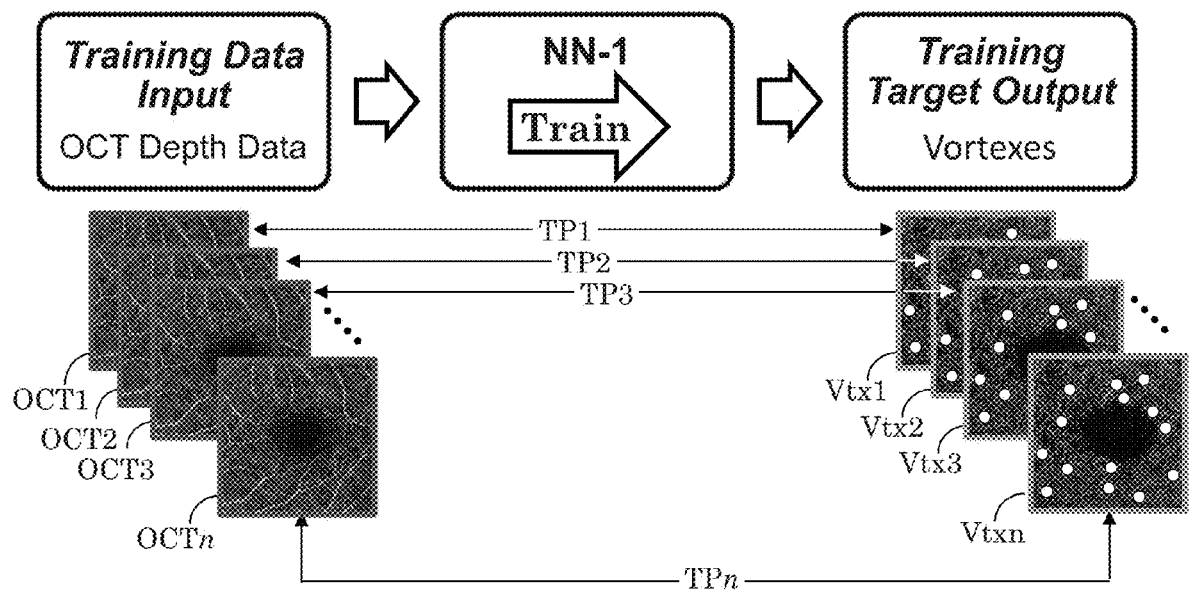
FIG. 17 illustrates an example of the training of a (e.g., convolutional or U-Net) neural network NN-1 in accord with the present invention.

For illustration purposes, FIG. 17 illustrates an example of the training of a neural network NN-1 (e.g., convolutional neural network or U-Net) in accord with the present invention. As discussed above, each training set may consist of training pairs TP1 to TPn, where each training pair may include OCT-based image/scan OCT1 to OCTn (e.g., OCT angiography data and/or structural OCT data) as a training input samples paired with corresponding, labeled OCT data Vtx1 to Vtxn. For ease of illustration, the training input OCT data is shown as color, depth-encoded en face slab/images, but it is to be understood that the training input OCT data may be volume data, B-scans, or A-scans. In the present example, neural network NN-1 is trained to identify vortices in the DCP, and so its target output Vtx1 to Vtxn has labeled vortices (e.g., white dots). Optionally, the training inputs OCT1 to OCTn may be limited to unlabeled DCP data corresponding to the labeled target outputs Vtx1 to Vtxn. In the present example, the neural network NN-1 is trained to extract the DCP data from the full OCT information, and so the training input in each training pair is shown to include the full scan information OCT1 to OCTn. Optionally, data augmentation methods may be used to increase the size of the training data, such as by dividing each of test input data (OCT1 to OCTn) into data segments (or image/scan patches) of smaller size. Generally, a larger training set size provides better training results.

Figure 18:
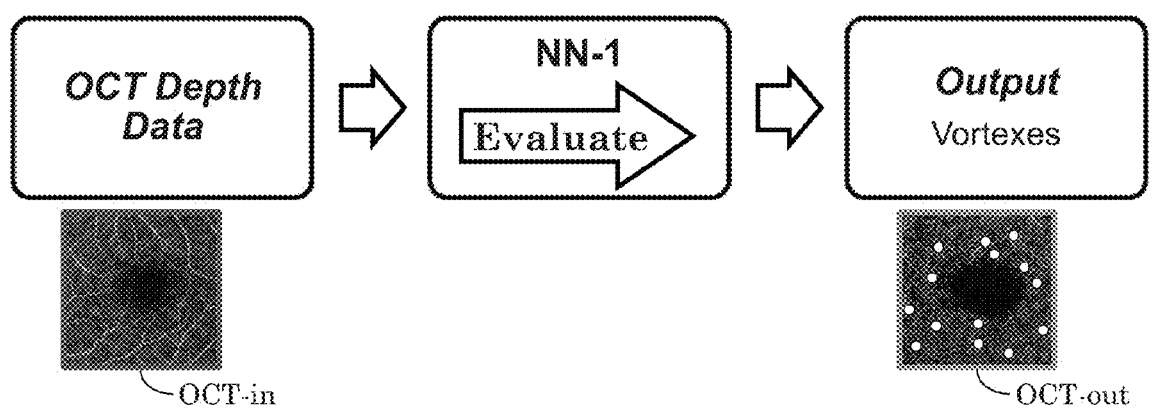
FIG. 18 illustrates an example operation of the neural network of FIG. 17, either with live data input after training or with test data input during an evaluation phase of a training session.

FIG. 18 illustrates an example operation of the neural network NN-1 of FIG. 17, either with live data input after training or with test data input during an evaluation phase of a training session. The present neural network NN-1 receives obtained OCT data (e.g., a live OCT/OCTA scan) as input OCT-in, and predicts (e.g. generates) a corresponding output image OCT-out with vortices in the DCP labeled, which may further be identified as veins. It is noted that input image OCT-in is not an image used in training, or an image derived from any image used in training. That is, OCT data (e.g., scan OCT-in) not seen before by the network NN-1 is selected for the testing/evaluation/operation phase.

Figure 19:
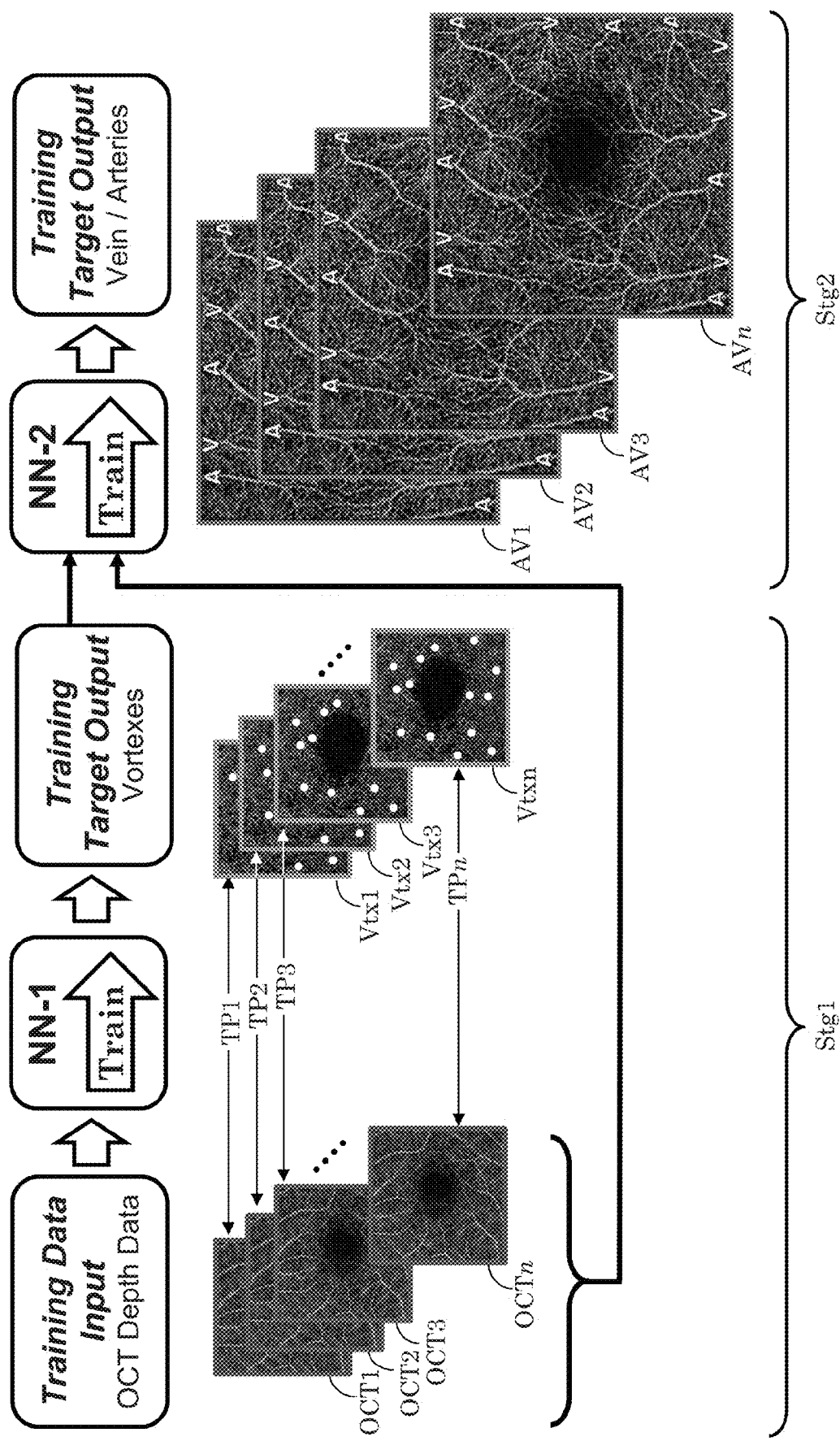
FIG. 19 illustrates an alternate training architecture that links in series multiple stages, each being an independent neural network.

FIG. 19 illustrates an alternate training architecture that links in series multiple NN stages, Stg1 and Stg2, each including its own neural network. The first stage Stg1 of the present architecture consists of a vortex-identification stage similar to that of FIG. 17. All elements in FIG. 19 similar to those of FIG. 17 have similar reference characters and are discussed above. In the present example, the output from vortex-identification stage Stg1 feeds into a second neural network NN-2 (e.g., second convolutional neural network and/or U-Net) of the second stage Stg2 for training. The training OCT data, OCT1 to OCTn, is also input to the second neural network NN-2. For example, an output from the vortex-identification stage Stg1 may be concatenated with (or appended to) its corresponding OCT training input, and both form the training input sample to the second neural network NN-2. The training target output AV1 to AVn may be the corresponding OCT data with labeled veins and/or arteries. In this manner, the present machine learning model learns to identify veins and arteries in two stages, wherein the first stage identifies vortices (or regions of vascular convergence), and the second stage applies the vortex information to OCT data to identify veins and/or arteries.

Figure 20:
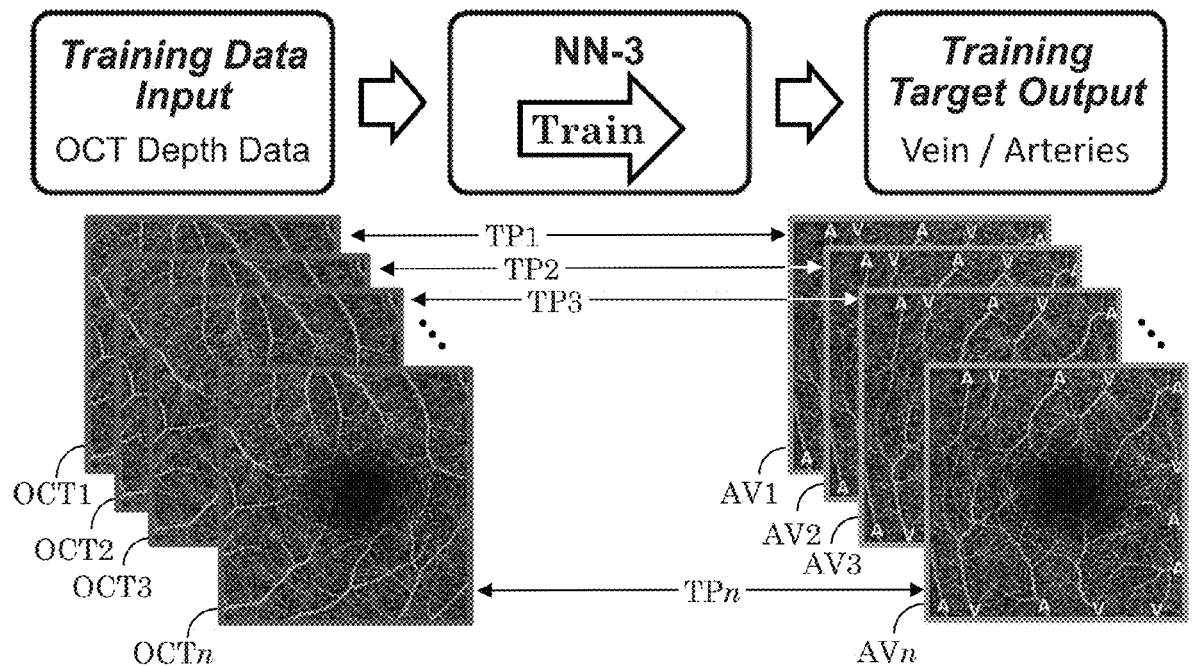
FIG. 20 illustrates an alternatively neural network training architecture wherein a neural network is trained to identify arteries and/or veins directly from input OCT data without an intermediate vortex identification stage.

FIG. 20 illustrates an alternatively neural network training architecture wherein a neural network NN-3 is trained to identify arteries and/or veins directly from input OCT data without an intermediate vortex identification stage. All elements in FIG. 20 similar to those of FIGS. 17 and 19 have similar reference characters and are discussed above.

CLINICAL EXAMPLES

Figure 21:
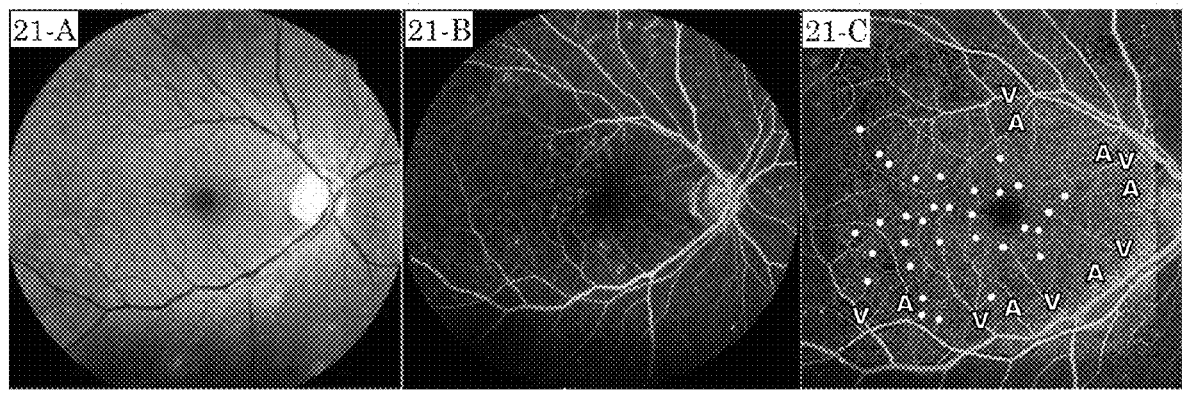
FIG. 21 illustrates how the present methods for distinguishing veins from arteries in OCT-based data facilitate analyses of how disease effects different vessel sub-types in diabetic retinopathy.

Distinguishing arteries from veins in (e.g., live) OCT/OCTA is of high clinical relevance since findings specific to each vessel type can add important information for detection and differentiation of many systemic and retinal diseases. For example, a 71-year-old female was seen for follow-up of long-standing non-proliferative diabetic retinopathy associated with diabetic macular edema. She had received focal laser treatment in the past, and more recently, intravitreal anti-vascular endothelial growth factor (VEGF) therapy, as needed. FIG. 21 illustrates how the present methods for distinguishing veins from arteries in OCT data facilitates analyses of how the disease effects different vessel subtypes. Color photograph 21-A shows microvascular abnormalities of diabetic retinopathy and evidence of prior focal laser for diabetic macular edema. Fluorescein angiography at 1 minute 30 seconds (image 21-B) shows scattered hyperfluorescent microaneurysms, staining laser scars, and minimal vascular leakage. A 9×9 mm color retina depth-encoded optical coherence tomography angiography study (image 21-C) is aligned to the FA image 21-B with veins labeled as "V" and arteries labeled as "A". Some of the deep venous vortices used to identify veins are marked with white dots. The OCTA identifies areas of reduced periarterial capillary density in the superior, temporal and inferior paramacular regions.

Figure 22:
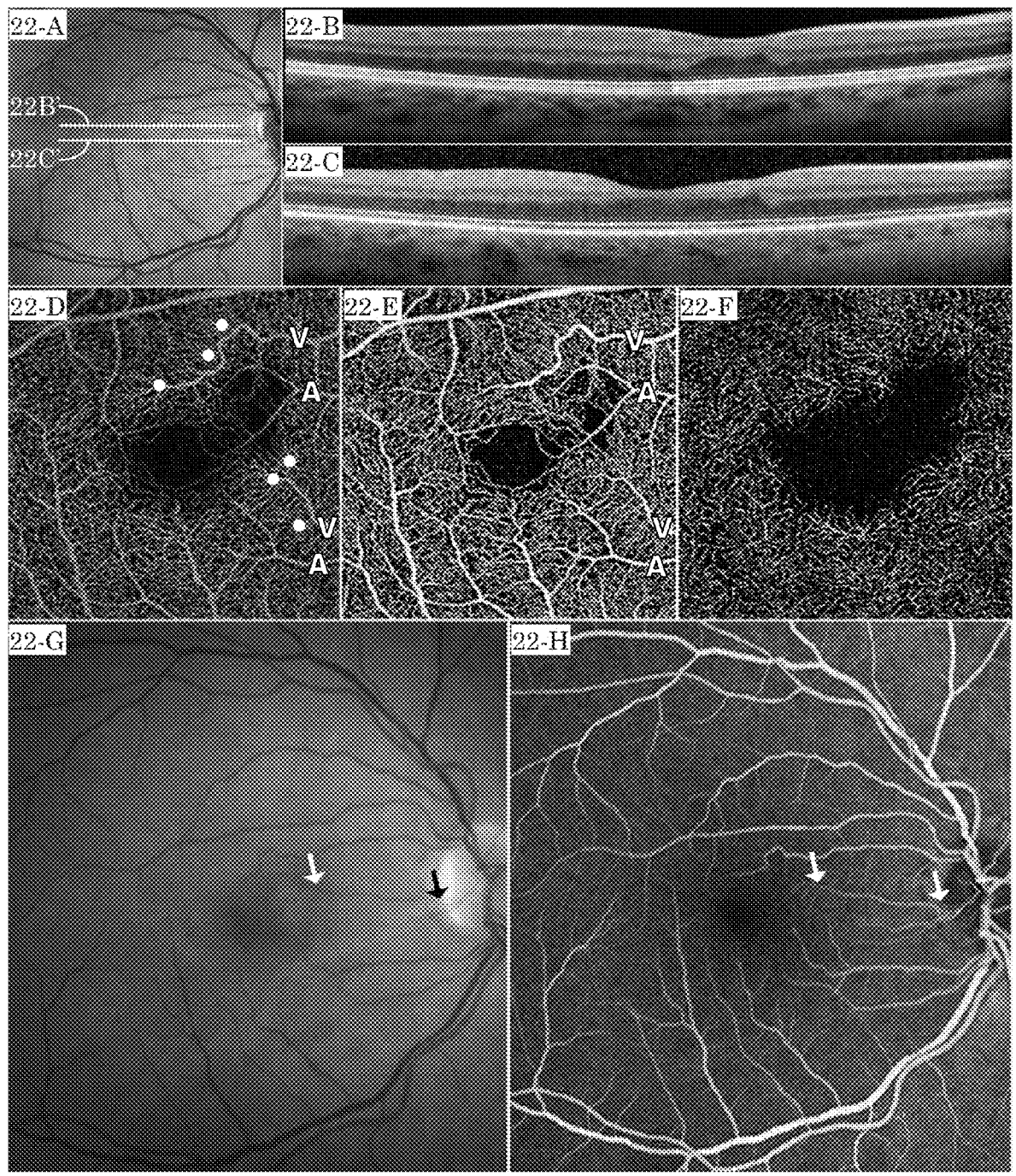
FIG. 22 illustrates a clinical example where the present invention made it possible to determine that a prior episode of cilioretinal artery hypoperfusion was responsible for producing OCTA findings consistent with a previous ischemic event of the deep vascular complex.

Identifying the nature of a prior retinal vascular occlusion was also studied. A 61-year-old female presented with the asymptomatic finding of localized thinning of the inner nuclear layer (INL) on OCT B-scans of the right eye was examined. The OCT pattern was consistent with resolved paracentral acute middle maculopathy (PAMM). As is shown in FIG. 22, using the present methods, it was possible to determine that a prior episode of cilioretinal artery hypoperfusion was responsible for producing OCT findings consistent with a previous ischemic event of the deep vascular complex. Near-infrared reflectance (image 22-A) shows no detectable lesion. Optical coherence tomography B-scans (images 22-B and 22-C) respectively corresponding to lines 22B' and 22C' in image 22-A show INL thinning with preserved outer retinal bands indicating resolved paracentral acute middle maculopathy (PAMM). The green vortices in the 3×3 mm color retina depth-encoded optical coherence tomography angiography (OCTA) image 22-D are used to distinguish veins (labeled "V") from arteries (labeled "A"). Some of the vortices used to identify veins are marked with white dots. Flow is better preserved in the superficial vascular plexus (image 22-E) than in the deep capillary plexus (image 22-F). The OCTA study is useful to show that the reduced flow is in a retinal area supplied by a small cilioretinal artery indicated with arrows on color fundus photography (22-G) and fluorescein angiography (22-H).

Figure 23:
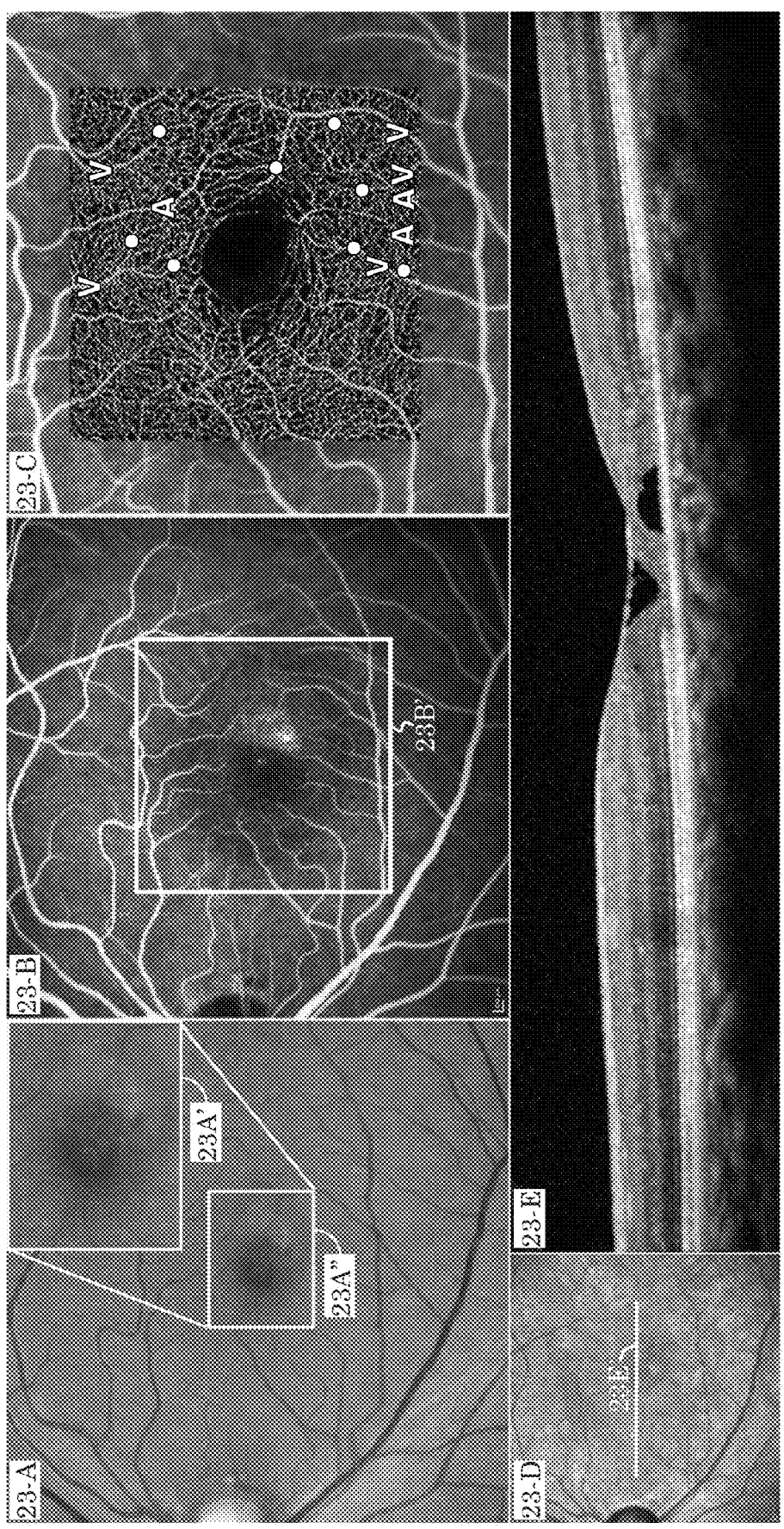
FIG. 23 illustrates a clinical example of macular telangiectasia type 2 where the present invention facilitated the determination that vascular damage was mostly concentrated around a vein draining, which shows the temporal aspect of the perifoveal capillary ring.

The vascular effects of macular telangiectasia type 2 were also explored. A 64-year-old female was referred for evaluation of bilateral metamorphopsia and reduce visual to 20/150 in the right eye and 20/50 in the left eye. The diagnosis of macular telangiectasia type 2 was made based upon characteristic clinical and imaging findings. As is evident from FIG. 23, using the present method, it can be determined that the vascular damage is mostly concentrated around a vein draining, which shows the temporal aspect of the perifoveal capillary ring. Color photograph 23-A, with enlargement 23A' of the foveal center (inset 23a"), shows loss of retinal transparency in the temporal fovea and a few small superficial retinal crystals. Fluorescein angiography (FA) at 1 minute 18 seconds (image 23-B) shows diffuse hyperfluorescence from the telangiectatic capillaries in the temporal fovea. The 3×3 mm color retina depth-encoded optical coherence tomography angiography image (image 23-C) aligned to the FA image (rectangle 23B' in in image 23-B) has veins labeled as "V" and arteries labeled as "A", with some of the vortices used to identify veins marked with white dots. The vascular damage is mostly concentrated around a vein draining the temporal aspect of the perifoveal capillary ring. Line 23E' in the near-infrared reflectance image (image 23-D) shows the location of a horizontal optical coherence tomography B-scan (image 23-E). The OCT B-scan shows central loss of both inner and outer retinal layers, hyporeflective intraretinal cavities, and preservation of a foveal depression.

Hereinafter is provided a description of various hardware and architectures suitable for the present invention.

Fundus Imaging System

Two categories of imaging systems used to image the fundus are flood illumination imaging systems (or flood illumination imagers) and scan illumination imaging systems (or scan imagers). Flood illumination imagers flood with light an entire field of view (FOV) of interest of a specimen at the same time, such as by use of a flash lamp, and capture a full-frame image of the specimen (e.g., the fundus) with a full-frame camera (e.g., a camera having a two-dimensional (2D) photo sensor array of sufficient size to capture the desired FOV, as a whole). For example, a flood illumination fundus imager would flood the fundus of an eye with light, and capture a full-frame image of the fundus in a single image capture sequence of the camera. A scan imager provides a scan beam that is scanned across a subject, e.g., an eye, and the scan beam is imaged at different scan positions as it is scanned across the subject creating a series of image-segments that may be reconstructed, e.g., montaged, to create a composite image of the desired FOV. The scan beam could be a point, a line, or a two-dimensional area such a slit or broad line.

Figure 24:
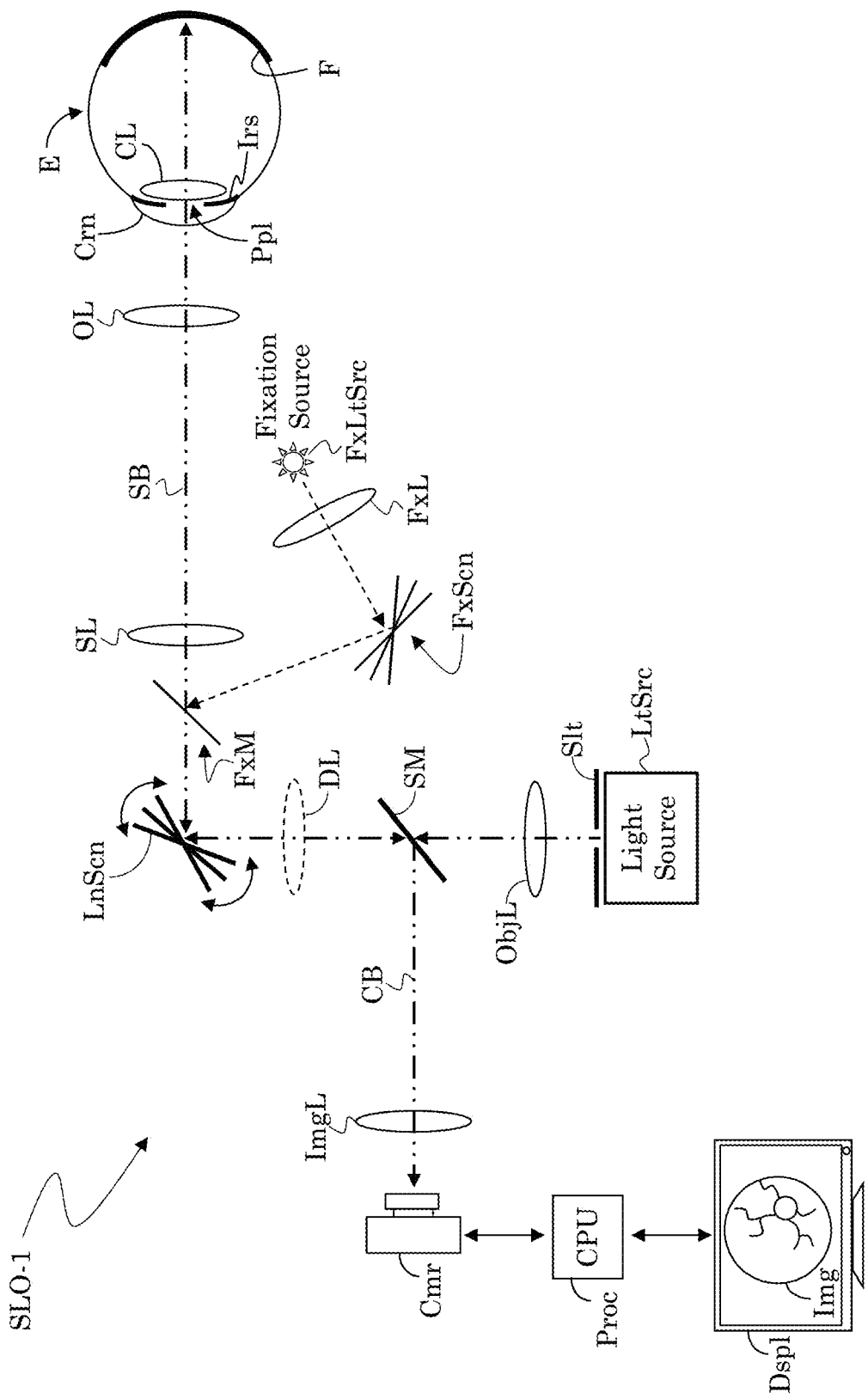
FIG. 24 illustrates an example of a slit scanning ophthalmic system for imaging a fundus.

FIG. 24 illustrates an example of a slit scanning ophthalmic system SLO-1 for imaging a fundus F, which is the interior surface of an eye E opposite the eye lens (or crystalline lens) CL and may include the retina, optic disc, macula, fovea, and posterior pole. In the present example, the imaging system is in a so-called "scan-descan" configuration, wherein a scanning line beam SB traverses the optical components of the eye E (including the cornea Crn, iris Irs, pupil Ppl, and crystalline lens CL) to be scanned across the fundus F. In the case of a flood fundus imager, no scanner is needed, and the light is applied across the entire, desired field of view (FOV) at once. Other scanning configurations are known in the art, and the specific scanning configuration is not critical to the present invention. As depicted, the imaging system includes one or more light sources LtSrc, preferably a multi-color LED system or a laser system in which the etendue has been suitably adjusted. An optional slit Slt (adjustable or static) is positioned in front of the light source LtSrc and may be used to adjust the width of the scanning line beam SB. Additionally, slit Slt may remain static during imaging or may be adjusted to different widths to allow for different confocality levels and different applications either for a particular scan or during the scan for use in suppressing reflexes. An optional objective lens ObjL may be placed in front of the slit Slt. The objective lens ObjL can be any one of state-of-the-art lenses including but not limited to refractive, diffractive, reflective, or hybrid lenses/systems. The light from slit Slt passes through a pupil splitting mirror SM and is directed towards a scanner LnScn. It is desirable to bring the scanning plane and the pupil plane as near together as possible to reduce vignetting in the system. Optional optics DL may be included to manipulate the optical distance between the images of the two components. Pupil splitting mirror SM may pass an illumination beam from light source LtSrc to scanner LnScn, and reflect a detection beam from scanner LnScn (e.g., reflected light returning from eye E) toward a camera Cmr. A task of the pupil splitting mirror SM is to split the illumination and detection beams and to aid in the suppression of system reflexes. The scanner LnScn could be a rotating galvo scanner or other types of scanners (e.g., piezo or voice coil, micro-electromechanical system (MEMS) scanners, electro-optical deflectors, and/or rotating polygon scanners). Depending on whether the pupil splitting is done before or after the scanner LnScn, the scanning could be broken into two steps wherein one scanner is in an illumination path and a separate scanner is in a detection path. Specific pupil splitting arrangements are described in detail in U.S. Pat. No. 9,456,746, which is herein incorporated in its entirety by reference.

From the scanner LnScn, the illumination beam passes through one or more optics, in this case a scanning lens SL and an ophthalmic or ocular lens OL, that allow for the pupil of the eye E to be imaged to an image pupil of the system. Generally, the scan lens SL receives a scanning illumination beam from the scanner LnScn at any of multiple scan angles (incident angles), and produces scanning line beam SB with a substantially flat surface focal plane (e.g., a collimated light path). Ophthalmic lens OL may focus the scanning line beam SB onto the fundus F (or retina) of eye E and image the fundus. In this manner, scanning line beam SB creates a traversing scan line that travels across the fundus F. One possible configuration for these optics is a Kepler type telescope wherein the distance between the two lenses is selected to create an approximately telecentric intermediate fundus image (4-$f$ configuration). The ophthalmic lens OL could be a single lens, an achromatic lens, or an arrangement of different lenses. All lenses could be refractive, diffractive, reflective or hybrid as known to one skilled in the art. The focal length(s) of the ophthalmic lens OL, scan lens SL and the size and/or form of the pupil splitting mirror SM and scanner LnScn could be different depending on the desired field of view (FOV), and so an arrangement in which multiple components can be switched in and out of the beam path, for example by using a flip in optic, a motorized wheel, or a detachable optical element, depending on the field of view can be envisioned. Since the field of view change results in a different beam size on the pupil, the pupil splitting can also be changed in conjunction with the change to the FOV. For example, a 45° to 60° field of view is a typical, or standard, FOV for fundus cameras. Higher fields of view, e.g., a widefield FOV, of 60°-120°, or more, may also be feasible. A widefield FOV may be desired for a combination of the Broad-Line Fundus Imager (BLFI) with another imaging modalities such as optical coherence tomography (OCT). The upper limit for the field of view may be determined by the accessible working distance in combination with the physiological conditions around the human eye. Because a typical human retina has a FOV of 140° horizontal and 80°-100° vertical, it may be desirable to have an asymmetrical field of view for the highest possible FOV on the system.

The scanning line beam SB passes through the pupil Ppl of the eye E and is directed towards the retinal, or fundus, surface F. The scanner LnScn1 adjusts the location of the light on the retina, or fundus, F such that a range of transverse locations on the eye E are illuminated. Reflected or scattered light (or emitted light in the case of fluorescence imaging) is directed back along as similar path as the illumination to define a collection beam CB on a detection path to camera Cmr.

In the "scan-descan" configuration of the present, exemplary slit scanning ophthalmic system SLO-1, light returning from the eye E is "descanned" by scanner LnScn on its way to pupil splitting mirror SM. That is, scanner LnScn scans the illumination beam from pupil splitting mirror SM to define the scanning illumination beam SB across eye E, but since scanner LnScn also receives returning light from eye E at the same scan position, scanner LnScn has the effect of descanning the returning light (e.g., cancelling the scanning action) to define a non-scanning (e.g., steady or stationary) collection beam from scanner LnScn to pupil splitting mirror SM, which folds the collection beam toward camera Cmr. At the pupil splitting mirror SM, the reflected light (or emitted light in the case of fluorescence imaging) is separated from the illumination light onto the detection path directed towards camera Cmr, which may be a digital camera having a photo sensor to capture an image. An imaging (e.g., objective) lens ImgL may be positioned in the detection path to image the fundus to the camera Cmr. As is the case for objective lens ObjL, imaging lens ImgL may be any type of lens known in the art (e.g., refractive, diffractive, reflective or hybrid lens). Additional operational details, in particular, ways to reduce artifacts in images, are described in PCT Publication No. WO2016/124644, the contents of which are herein incorporated in their entirety by reference. The camera Cmr captures the received image, e.g., it creates an image file, which can be further processed by one or more (electronic) processors or computing devices (e.g., the computer system shown in FIG. 31). Thus, the collection beam (returning from all scan positions of the scanning line beam SB) is collected by the camera Cmr, and a full-frame image Img may be constructed from a composite of the individually captured collection beams, such as by montaging. However, other scanning configuration are also contemplated, including ones where the illumination beam is scanned across the eye E and the collection beam is scanned across a photo sensor array of the camera. PCT Publication WO 2012/059236 and US Patent Publication No. 2015/0131050, herein incorporated by reference, describe several embodiments of slit scanning ophthalmoscopes including various designs where the returning light is swept across the camera's photo sensor array and where the returning light is not swept across the camera's photo sensor array.

In the present example, the camera Cmr is connected to a processor (e.g., processing module) Proc and a display (e.g., displaying module, computer screen, electronic screen, etc.) Dspl, both of which can be part of the image system itself, or may be part of separate, dedicated processing and/or displaying unit(s), such as a computer system wherein data is passed from the camera Cmr to the computer system over a cable or computer network including wireless networks. The display and processor can be an all in one unit. The display can be a traditional electronic display/screen or of the touch screen type and can include a user interface for displaying information to and receiving information from an instrument operator, or user. The user can interact with the display using any type of user input device as known in the art including, but not limited to, mouse, knobs, buttons, pointer, and touch screen.

It may be desirable for a patient's gaze to remain fixed while imaging is carried out. One way to achieve this is to provide a fixation target that the patient can be directed to stare at. Fixation targets can be internal or external to the instrument depending on what area of the eye is to be imaged. One embodiment of an internal fixation target is shown in FIG. 24. In addition to the primary light source LtSrc used for imaging, a second optional light source FxLtSrc, such as one or more LEDs, can be positioned such that a light pattern is imaged to the retina using lens FxL, scanning element FxScn and reflector/mirror FxM. Fixation scanner FxScn can move the position of the light pattern and reflector FxM directs the light pattern from fixation scanner FxScn to the fundus F of eye E. Preferably, fixation scanner FxScn is position such that it is located at the pupil plane of the system so that the light pattern on the retina/fundus can be moved depending on the desired fixation location.

Slit-scanning ophthalmoscope systems are capable of operating in different imaging modes depending on the light source and wavelength selective filtering elements employed. True color reflectance imaging (imaging similar to that observed by the clinician when examining the eye using a hand-held or slit lamp ophthalmoscope) can be achieved when imaging the eye with a sequence of colored LEDs (red, blue, and green). Images of each color can be built up in steps with each LED turned on at each scanning position or each color image can be taken in its entirety separately. The three, color images can be combined to display the true color image, or they can be displayed individually to highlight different features of the retina. The red channel best highlights the choroid, the green channel highlights the retina, and the blue channel highlights the anterior retinal layers. Additionally, light at specific frequencies (e.g., individual colored LEDs or lasers) can be used to excite different fluorophores in the eye (e.g., autofluorescence) and the resulting fluorescence can be detected by filtering out the excitation wavelength.

The fundus imaging system can also provide an infrared reflectance image, such as by using an infrared laser (or other infrared light source). The infrared (IR) mode is advantageous in that the eye is not sensitive to the IR wavelengths. This may permit a user to continuously take images without disturbing the eye (e.g., in a preview/alignment mode) to aid the user during alignment of the instrument. Also, the IR wavelengths have increased penetration through tissue and may provide improved visualization of choroidal structures. In addition, fluorescein angiography (FA) and indocyanine green (ICG) angiography imaging can be accomplished by collecting images after a fluorescent dye has been injected into the subject's bloodstream.

Optical Coherence Tomography Imaging System

In addition to fundus photography, fundus auto-fluorescence (FAF), fluorescein angiography (FA), ophthalmic images may also be created by other imaging modalities, such as, optical coherence tomography (OCT), OCT angiography (OCTA), and/or ocular ultrasonography. The present invention, or at least portions of the present invention with minor modification(s) as it would be understood in the art, may be applied to these other ophthalmic imaging modalities. More specifically, the present invention may also be applied to ophthalmic images produces by an OCT/OCTA system producing OCT and/or OCTA images. For instance, the present invention may be applied to en face OCT/OCTA images. Examples of fundus imagers are provided in U.S. Pat. Nos. 8,967,806 and 8,998,411, examples of OCT systems are provided in U.S. Pat. Nos. 6,741,359 and 9,706,915, and examples of an OCTA imaging system may be found in U.S. Pat. Nos. 9,700,206 and 9,759,544, all of which are herein incorporated in their entirety by reference. For the sake of completeness, an exemplary OCT/OCTA system is provided herein.

Figure 25:
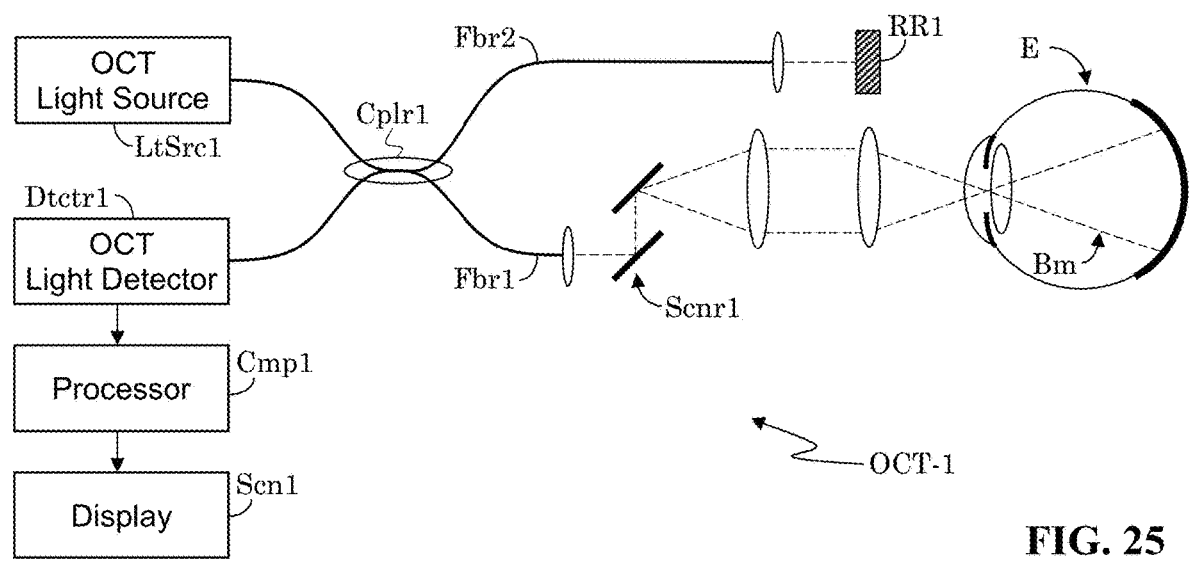
FIG. 25 illustrates a generalized frequency domain optical coherence tomography system used to collect 3-D image data of the eye suitable for use with the present invention.

FIG. 25 illustrates a generalized frequency domain optical coherence tomography (FD-OCT) system used to collect 3-D image data of the eye suitable for use with the present invention. An FD-OCT system OCT_1 includes a light source, LtSrc1. Typical light sources include, but are not limited to, broadband light sources with short temporal coherence lengths or swept laser sources. A beam of light from light source LtSrc1 is routed, typically by optical fiber Fbr1, to illuminate a sample, e.g., eye E; a typical sample being tissues in the human eye. The light source LrSrc1 can be either a broadband light source with short temporal coherence length in the case of spectral domain OCT (SD-OCT) or a wavelength tunable laser source in the case of swept source OCT (SS-OCT). The light may be scanned, typically with a scanner Scnr1 between the output of the optical fiber Fbr1 and the sample E, so that the beam of light (dashed line Bm) is scanned laterally (in x and y) over the region of the sample to be imaged. In the case of a full-field OCT, no scanner is needed and the light is applied across the entire, desired field of view (FOV) at once. Light scattered from the sample is collected, typically into the same optical fiber Fbr1 used to route the light for illumination. Reference light derived from the same light source LtSrc1 travels a separate path, in this case involving optical fiber Fbr2 and retro-reflector RR1 with an adjustable optical delay. Those skilled in the art will recognize that a transmissive reference path can also be used and that the adjustable delay could be placed in the sample or reference arm of the interferometer. Collected sample light is combined with reference light, typically in a fiber coupler Cplr1, to form light interference in an OCT light detector Dtctr1 (e.g., photodetector array, digital camera, etc.). Although a single fiber port is shown going to the detector Dtctr1, those skilled in the art will recognize that various designs of interferometers can be used for balanced or unbalanced detection of the interference signal. The output from the detector Dtctr1 is supplied to a processor Cmp1 (e.g., computing device) that converts the observed interference into depth information of the sample. The depth information may be stored in a memory associated with the processor Cmp1 and/or displayed on a display (e.g., computer/electronic display/screen) Scn1. The processing and storing functions may be localized within the OCT instrument or functions may be performed on an external processing unit (e.g., the computer system shown in FIG. 31) to which the collected data is transferred. This unit could be dedicated to data processing or perform other tasks which are quite general and not dedicated to the OCT device. The processor Cmp1 may contain, for example, a field-programmable gate array (FPGA), a digital signal processor (DSP), an application specific integrated circuit (ASIC), a graphics processing unit (GPU), a system on chip (SoC), a central processing unit (CPU), a general purpose graphics processing unit (GPGPU), or a combination thereof, that performs some, or the entire data processing steps, prior to passing on to the host processor or in a parallelized fashion.

The sample and reference arms in the interferometer could consist of bulk-optics, fiber-optics, or hybrid bulk-optic systems and could have different architectures such as Michelson, Mach-Zehnder or common-path based designs as would be known by those skilled in the art. Light beam as used herein should be interpreted as any carefully directed light path. Instead of mechanically scanning the beam, a field of light can illuminate a one or two-dimensional area of the retina to generate the OCT data (see for example, U.S. Pat. No. 9,332,902; D. Hillmann et al, "Holoscopy—holographic optical coherence tomography" Optics Letters 36(13): 2390 2011; Y. Nakamura, et al, "High-Speed three dimensional human retinal imaging by line field spectral domain optical coherence tomography" Optics Express 15(12):7103 2007; Blazkiewicz et al, "Signal-to-noise ratio study of full-field Fourier-domain optical coherence tomography" Applied Optics 44(36):7722 (2005)). In time-domain systems, the reference arm needs to have a tunable optical delay to generate interference. Balanced detection systems are typically used in TD-OCT and SS-OCT systems, while spectrometers are used at the detection port for SD-OCT systems. The invention described herein could be applied to any type of OCT system. Various aspects of the invention could apply to any type of OCT system or other types of ophthalmic diagnostic systems and/or multiple ophthalmic diagnostic systems including but not limited to fundus imaging systems, visual field test devices, and scanning laser polarimeters.

In Fourier Domain optical coherence tomography (FD-OCT), each measurement is the real-valued spectral interferogram (Sj(k)). The real-valued spectral data typically goes through several post-processing steps including background subtraction, dispersion correction, etc. The Fourier transform of the processed interferogram, results in a complex valued OCT signal output $Aj(z)=|Aj|ei\varphi$. The absolute value of this complex OCT signal, $|Aj|$, reveals the profile of scattering intensities at different path lengths, and therefore scattering as a function of depth (z-direction) in the sample. Similarly, the phase, $\varphi j$ can also be extracted from the complex valued OCT signal. The profile of scattering as a function of depth is called an axial scan (A-scan). A set of A-scans measured at neighboring locations in the sample produces a cross-sectional image (tomogram or B-scan) of the sample. A collection of B-scans collected at different transverse locations on the sample makes up a data volume or cube. For a particular volume of data, the term fast axis refers to the scan direction along a single B-scan whereas slow axis refers to the axis along which multiple B-scans are collected. The term "cluster scan" may refer to a single unit or block of data generated by repeated acquisitions at the same (or substantially the same) location (or region) for the purposes of analyzing motion contrast, which may be used to identify blood flow. A cluster scan can consist of multiple A-scans or B-scans collected with relatively short time separations at approximately the same location(s) on the sample. Since the scans in a cluster scan are of the same region, static structures remain relatively unchanged from scan to scan within the cluster scan, whereas motion contrast between the scans that meets predefined criteria may be identified as blood flow. A variety of ways to create B-scans are known in the art including but not limited to: along the horizontal or x-direction, along the vertical or y-direction, along the diagonal of x and y, or in a circular or spiral pattern. B-scans may be in the x-z dimensions but may be any cross-sectional image that includes the z-dimension.

In OCT Angiography, or Functional OCT, analysis algorithms may be applied to OCT data collected at the same, or approximately the same, sample locations on a sample at different times (e.g., a cluster scan) to analyze motion or flow (see for example US Patent Publication Nos. 2005/0171438, 2012/0307014, 2010/0027857, 2012/0277579 and U.S. Pat. No. 6,549,801, all of which are herein incorporated in their entirety by reference). An OCT system may use any one of a number of OCT angiography processing algorithms (e.g., motion contrast algorithms) to identify blood flow. For example, motion contrast algorithms can be applied to the intensity information derived from the image data (intensity-based algorithm), the phase information from the image data (phase-based algorithm), or the complex image data (complex-based algorithm). An en face image is a 2D projection of 3D OCT data (e.g., by averaging the intensity of each individual A-scan, such that each A-scan defines a pixel in the 2D projection). Similarly, an en face vasculature image is an image displaying motion contrast signal in which the data dimension corresponding to depth (e.g., z-direction along an A-scan) is displayed as a single representative value (e.g., a pixel in a 2D projection image), typically by summing or integrating all or an isolated portion of the data (see for example U.S. Pat. No. 7,301,644 herein incorporated in its entirety by reference). OCT systems that provide an angiography imaging functionality may be termed OCT angiography (OCTA) systems.

Figure 26:
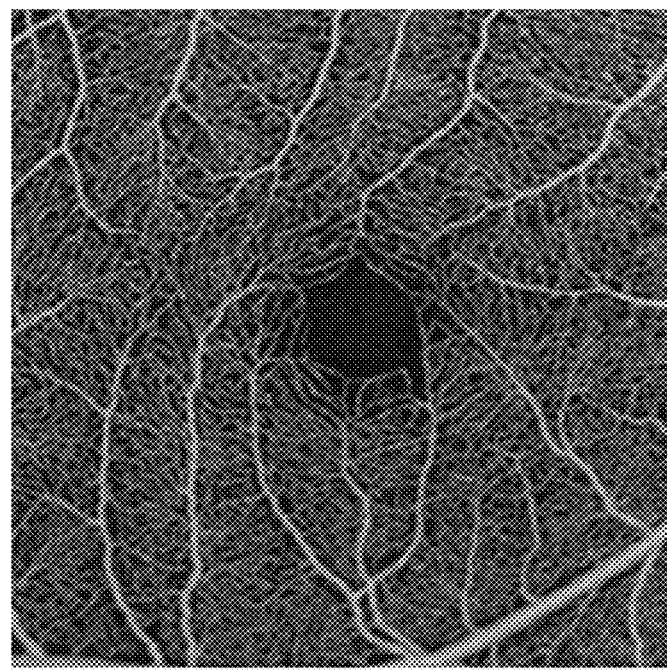
FIG. 26 shows an example of an en face vasculature image.

FIG. 26 shows an example of an en face vasculature image. After processing the data to highlight motion contrast using any of the motion contrast techniques known in the art, a range of pixels corresponding to a given tissue depth from the surface of internal limiting membrane (ILM) in retina, may be summed to generate the en face (e.g., frontal view) image of the vasculature.

Neural Networks

As discussed above, the present invention may use a neural network (NN) machine learning (ML) model. For the sake of completeness, a general discussion of neural networks is provided herein. The present invention may use any, singularly or in combination, of the below described neural network architecture(s). A neural network, or neural net, is a (nodal) network of interconnected neurons, where each neuron represents a node in the network. Groups of neurons may be arranged in layers, with the outputs of one layer feeding forward to a next layer in a multilayer perceptron (MLP) arrangement. MLP may be understood to be a feedforward neural network model that maps a set of input data onto a set of output data.

Figure 27:
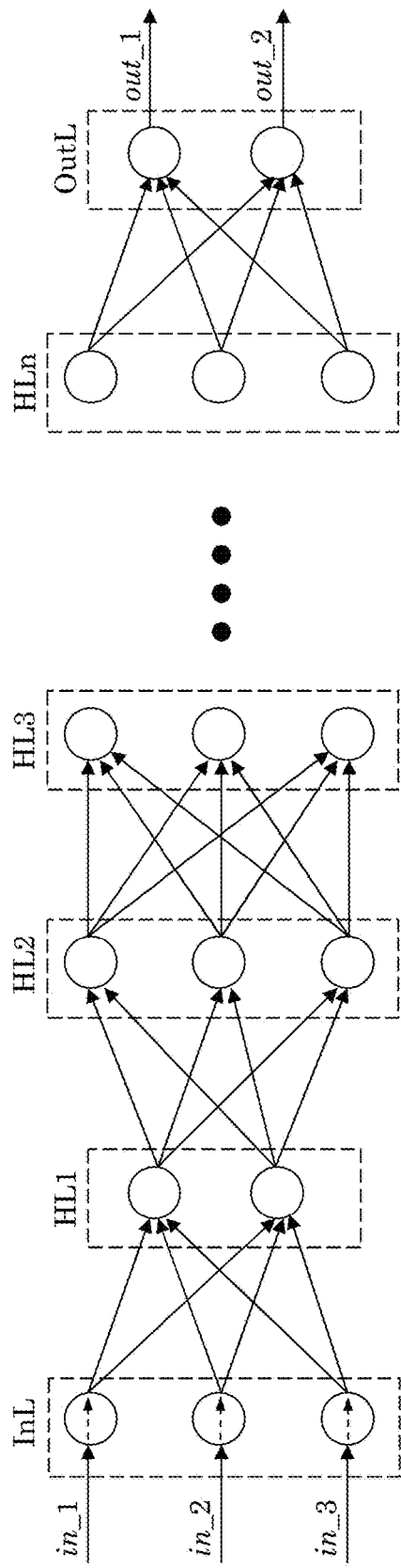
FIG. 27 illustrates an example of a multilayer perceptron (MLP) neural network.

FIG. 27 illustrates an example of a multilayer perceptron (MLP) neural network. Its structure may include multiple hidden (e.g., internal) layers HL1 to HLn that map an input layer InL (that receives a set of inputs (or vector input) in_1 to in_3) to an output layer OutL that produces a set of outputs (or vector output), e.g., out_1 and out_2. Each layer may have any given number of nodes, which are herein illustratively shown as circles within each layer. In the present example, the first hidden layer HL1 has two nodes, while hidden layers HL2, HL3, and HLn each have three nodes. Generally, the deeper the MLP (e.g., the greater the number of hidden layers in the MLP), the greater its capacity to learn. The input layer InL receives a vector input (illustratively shown as a three-dimensional vector consisting of in_1, in_2 and in_3), and may apply the received vector input to the first hidden layer HL1 in the sequence of hidden layers. An output layer OutL receives the output from the last hidden layer, e.g., HLn, in the multilayer model, processes its inputs, and produces a vector output result (illustratively shown as a two-dimensional vector consisting of out_1 and out_2).

Typically, each neuron (or node) produces a single output that is fed forward to neurons in the layer immediately following it. But each neuron in a hidden layer may receive multiple inputs, either from the input layer or from the outputs of neurons in an immediately preceding hidden layer. In general, each node may apply a function to its inputs to produce an output for that node. Nodes in hidden layers (e.g., learning layers) may apply the same function to their respective input(s) to produce their respective output(s). Some nodes, however, such as the nodes in the input layer InL receive only one input and may be passive, meaning that they simply relay the values of their single input to their output(s), e.g., they provide a copy of their input to their output(s), as illustratively shown by dotted arrows within the nodes of input layer InL.

Figure 28:
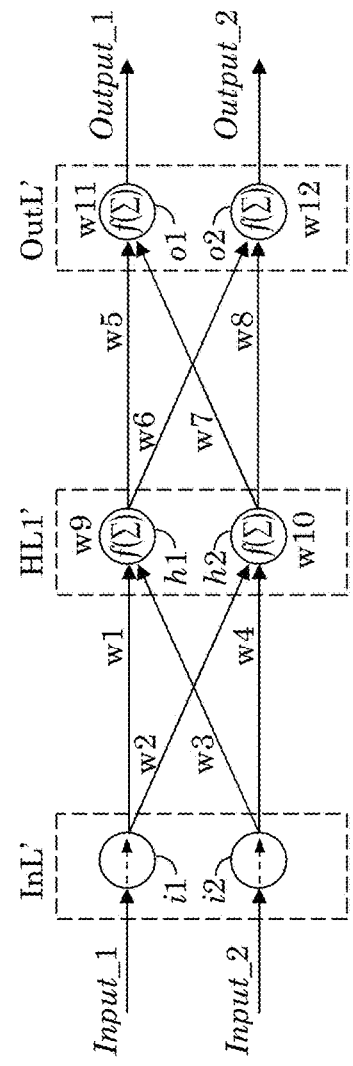
FIG. 28 shows a simplified neural network consisting of an input layer, a hidden layer, and an output layer.

For illustration purposes, FIG. 28 shows a simplified neural network consisting of an input layer InL', a hidden layer HL1', and an output layer OutL'. Input layer InL' is shown having two input nodes i1 and i2 that respectively receive inputs Input_1 and Input_2 (e.g. the input nodes of layer InL' receive an input vector of two dimensions). The input layer InL' feeds forward to one hidden layer HL1' having two nodes h1 and h2, which in turn feeds forward to an output layer OutL' of two nodes o1 and o2. Interconnections, or links, between neurons (illustrative shown as solid arrows) have weights w1 to w8. Typically, except for the input layer, a node (neuron) may receive as input the outputs of nodes in its immediately preceding layer. Each node may calculate its output by multiplying each of its inputs by each input's corresponding interconnection weight, summing the products of it inputs, adding (or multiplying by) a constant defined by another weight or bias that may be associated with that particular node (e.g., node weights w9, w10, w11, w12 respectively corresponding to nodes h1, h2, o1, and o2), and then applying a non-linear function or logarithmic function to the result. The non-linear function may be termed an activation function or transfer function. Multiple activation functions are known the art, and selection of a specific activation function is not critical to the present discussion. It is noted, however, that operation of the ML model, or behavior of the neural net, is dependent upon weight values, which may be learned so that the neural network provides a desired output for a given input.

The neural net learns (e.g., is trained to determine) appropriate weight values to achieve a desired output for a given input during a training, or learning, stage. Before the neural net is trained, each weight may be individually assigned an initial (e.g., random and optionally non-zero) value, e.g. a random-number seed. Various methods of assigning initial weights are known in the art. The weights are then trained (optimized) so that for a given training vector input, the neural network produces an output close to a desired (predetermined) training vector output. For example, the weights may be incrementally adjusted in thousands of iterative cycles by a technique termed back-propagation. In each cycle of back-propagation, a training input (e.g., vector input or training input image/sample) is fed forward through the neural network to determine its actual output (e.g., vector output). An error for each output neuron, or output node, is then calculated based on the actual neuron output and a target training output for that neuron (e.g., a training output image/sample corresponding to the present training input image/sample). One then propagates back through the neural network (in a direction from the output layer back to the input layer) updating the weights based on how much effect each weight has on the overall error so that the output of the neural network moves closer to the desired training output. This cycle is then repeated until the actual output of the neural network is within an acceptable error range of the desired training output for the given training input. As it would be understood, each training input may require many back-propagation iterations before achieving a desired error range. Typically, an epoch refers to one back-propagation iteration (e.g., one forward pass and one backward pass) of all the training samples, such that training a neural network may require many epochs. Generally, the larger the training set, the better the performance of the trained ML model, so various data augmentation methods may be used to increase the size of the training set. For example, when the training set includes pairs of corresponding training input images and training output images, the training images may be divided into multiple corresponding image segments (or patches). Corresponding patches from a training input image and training output image may be paired to define multiple training patch pairs from one input/output image pair, which enlarges the training set. Training on large training sets, however, places high demands on computing resources, e.g. memory and data processing resources. Computing demands may be reduced by dividing a large training set into multiple mini-batches, where the mini-batch size defines the number of training samples in one forward/backward pass. In this case, and one epoch may include multiple mini-batches. Another issue is the possibility of a NN overfitting a training set such that its capacity to generalize from a specific input to a different input is reduced. Issues of overfitting may be mitigated by creating an ensemble of neural networks or by randomly dropping out nodes within a neural network during training, which effectively removes the dropped nodes from the neural network. Various dropout regulation methods, such as inverse dropout, are known in the art.

It is noted that the operation of a trained NN machine model is not a straight-forward algorithm of operational/analyzing steps. Indeed, when a trained NN machine model receives an input, the input is not analyzed in the traditional sense. Rather, irrespective of the subject or nature of the input (e.g., a vector defining a live image/scan or a vector defining some other entity, such as a demographic description or a record of activity) the input will be subjected to the same predefined architectural construct of the trained neural network (e.g., the same nodal/layer arrangement, trained weight and bias values, predefined convolution/deconvolution operations, activation functions, pooling operations, etc.), and it may not be clear how the trained network's architectural construct produces its output. Furthermore, the values of the trained weights and biases are not deterministic and depend upon many factors, such as the amount of time the neural network is given for training (e.g., the number of epochs in training), the random starting values of the weights before training starts, the computer architecture of the machine on which the NN is trained, selection of training samples, distribution of the training samples among multiple mini-batches, choice of activation function(s), choice of error function(s) that modify the weights, and even if training is interrupted on one machine (e.g., having a first computer architecture) and completed on another machine (e.g., having a different computer architecture). The point is that the reasons why a trained ML model reaches certain outputs is not clear, and much research is currently ongoing to attempt to determine the factors on which a ML model bases its outputs. Therefore, the processing of a neural network on live data cannot be reduced to a simple algorithm of steps. Rather, its operation is dependent upon its training architecture, training sample sets, training sequence, and various circumstances in the training of the ML model.

In summary, construction of a NN machine learning model may include a learning (or training) stage and a classification (or operational) stage. In the learning stage, the neural network may be trained for a specific purpose and may be provided with a set of training examples, including training (sample) inputs and training (sample) outputs, and optionally including a set of validation examples to test the progress of the training. During this learning process, various weights associated with nodes and node-interconnections in the neural network are incrementally adjusted in order to reduce an error between an actual output of the neural network and the desired training output. In this manner, a multi-layer feed-forward neural network (such as discussed above) may be made capable of approximating any measurable function to any desired degree of accuracy. The result of the learning stage is a (neural network) machine learning (ML) model that has been learned (e.g., trained). In the operational stage, a set of test inputs (or live inputs) may be submitted to the learned (trained) ML model, which may apply what it has learned to produce an output prediction based on the test inputs.

Like the regular neural networks of FIGS. 26 and 27, convolutional neural networks (CNN) are also made up of neurons that have learnable weights and biases. Each neuron receives inputs, performs an operation (e.g., dot product), and is optionally followed by a non-linearity. The CNN, however, may receive raw image pixels at one end (e.g., the input end) and provide classification (or class) scores at the other end (e.g., the output end). Because CNNs expect an image as input, they are optimized for working with volumes (e.g., pixel height and width of an image, plus the depth of the image, e.g., color depth such as an RGB depth defined of three colors: red, green, and blue). For example, the layers of a CNN may be optimized for neurons arranged in 3 dimensions. The neurons in a CNN layer may also be connected to a small region of the layer before it, instead of all of the neurons in a fully-connected NN. The final output layer of a CNN may reduce a full image into a single vector (classification) arranged along the depth dimension.

Figure 29:
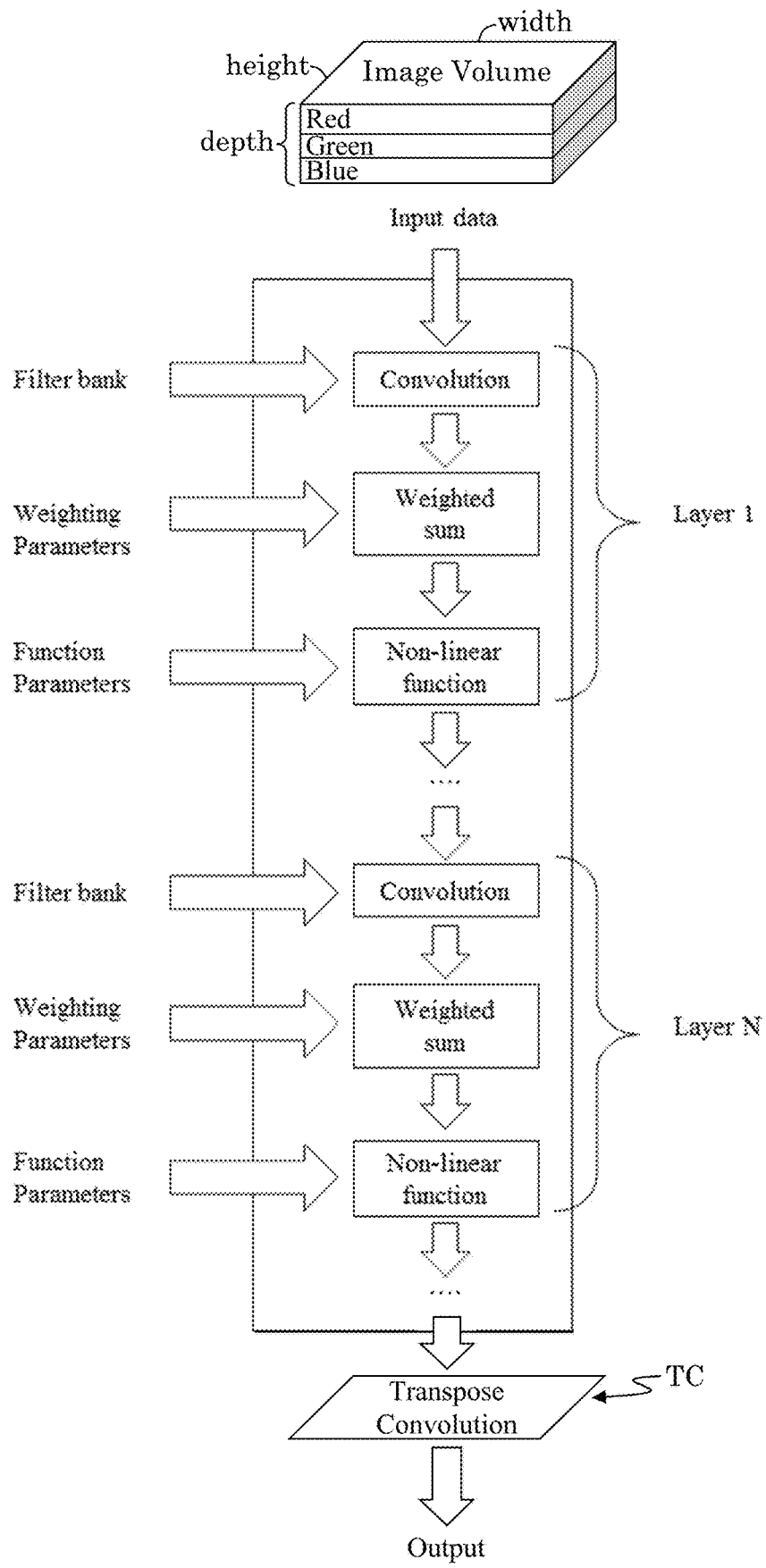
FIG. 29 illustrates an example convolutional neural network architecture.

FIG. 29 provides an example convolutional neural network architecture. A convolutional neural network may be defined as a sequence of two or more layers (e.g., Layer 1 to Layer N), where a layer may include a (image) convolution step, a weighted sum (of results) step, and a non-linear function step. The convolution may be performed on its input data by applying a filter (or kernel), e.g. on a moving window across the input data, to produce a feature map. Each layer and component of a layer may have different pre-determined filters (from a filter bank), weights (or weighting parameters), and/or function parameters. In the present example, the input data is an image, which may be raw pixel values of the image, of a given pixel height and width. In the present example, the input image is illustrated as having a depth of three color channels RGB (Red, Green, and Blue). Optionally, the input image may undergo various preprocessing, and the preprocessing results may be input in place of, or in addition to, the raw input image. Some examples of image preprocessing may include: retina blood vessel map segmentation, color space conversion, adaptive histogram equalization, connected components generation, etc. Within a layer, a dot product may be computed between the given weights and a small region they are connected to in the input volume. Many ways of configuring a CNN are known in the art, but as an example, a layer may be configured to apply an elementwise activation function, such as max (0,x) thresholding at zero. A pooling function may be performed (e.g., along the x-y directions) to down-sample a volume. A fully-connected layer may be used to determine the classification output and produce a one-dimensional output vector, which has been found useful for image recognition and classification. However, for image segmentation, the CNN would need to classify each pixel. Since each CNN layers tends to reduce the resolution of the input image, another stage is needed to up-sample the image back to its original resolution. This may be achieved by application of a transpose convolution (or deconvolution) stage TC, which typically does not use any predefine interpolation method, and instead has learnable parameters.

Convolutional Neural Networks have been successfully applied to many computer vision problems. As explained above, training a CNN generally requires a large training dataset. The U-Net architecture is based on CNNs and can generally can be trained on a smaller training dataset than conventional CNNs.

Figure 30:
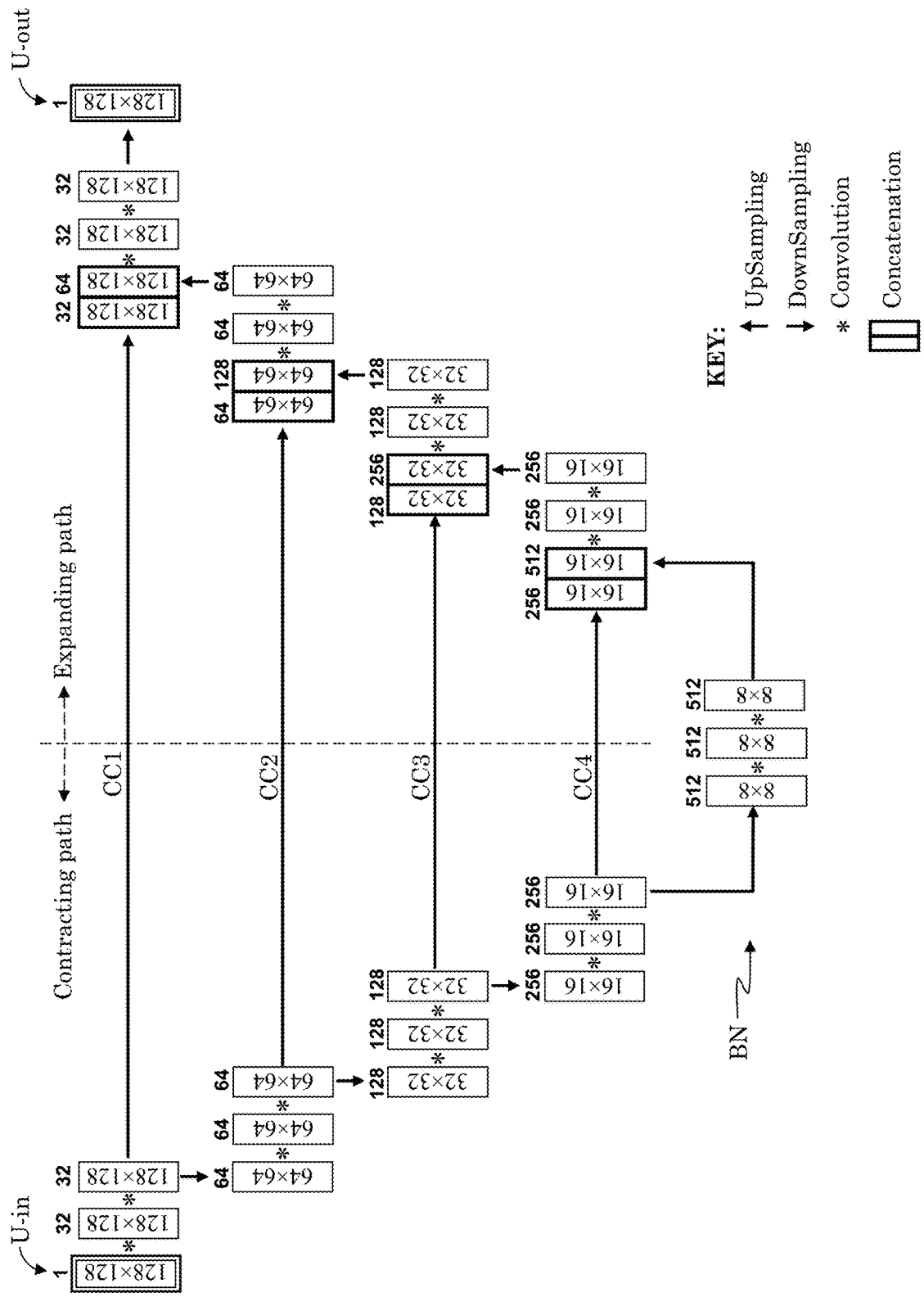
FIG. 30 illustrates an example U-Net architecture.

FIG. 30 illustrates an example U-Net architecture. The present exemplary U-Net includes an input module (or input layer or stage) that receives an input U-in (e.g., input image or image patch) of any given size. For illustration purposes, the image size at any stage, or layer, is indicated within a box that represents the image, e.g., the input module encloses number "128×128" to indicate that input image U-in is comprised of 128 by 128 pixels. The input image may be a fundus image, an OCT/OCTA en face, B-scan image, etc. It is to be understood, however, that the input may be of any size or dimension. For example, the input image may be an RGB color image, monochrome image, volume image, etc. The input image undergoes a series of processing layers, each of which is illustrated with exemplary sizes, but these sizes are illustration purposes only and would depend, for example, upon the size of the image, convolution filter, and/or pooling stages. The present architecture consists of a contracting path (herein illustratively comprised of four encoding modules) followed by an expanding path (herein illustratively comprised of four decoding modules), and copy-and-crop links (e.g., CC1 to CC4) between corresponding modules/stages that copy the output of one encoding module in the contracting path and concatenates it to (e.g., appends it to the back of) the up-converted input of a correspond decoding module in the expanding path. This results in a characteristic U-shape, from which the architecture draws its name. Optionally, such as for computational considerations, a "bottleneck" module/stage (BN) may be positioned between the contracting path and the expanding path. The bottleneck BN may consist of two convolutional layers (with batch normalization and optional dropout).

The contracting path is similar to an encoder, and generally captures context (or feature) information by the use of feature maps. In the present example, each encoding module in the contracting path may include two or more convolutional layers, illustratively indicated by an asterisk symbol "*", and which may be followed by a max pooling layer (e.g., DownSampling layer). For example, input image U-in is illustratively shown to undergo two convolution layers, each with 32 feature maps. As it would be understood, each convolution kernel produces a feature map (e.g., the output from a convolution operation with a given kernel is an image typically termed a "feature map"). For example, input U-in undergoes a first convolution that applies 32 convolution kernels (not shown) to produce an output consisting of 32 respective feature maps. However, as it is known in the art, the number of feature maps produced by a convolution operation may be adjusted (up or down). For example, the number of feature maps may be reduced by averaging groups of feature maps, dropping some feature maps, or other known method of feature map reduction. In the present example, this first convolution is followed by a second convolution whose output is limited to 32 feature maps. Another way to envision feature maps may be to think of the output of a convolution layer as a 3D image whose 2D dimension is given by the listed X-Y planar pixel dimension (e.g., 128×128 pixels), and whose depth is given by the number of feature maps (e.g., 32 planar images deep). Following this analogy, the output of the second convolution (e.g., the output of the first encoding module in the contracting path) may be described as a 128×128×32 image.

The output from the second convolution then undergoes a pooling operation, which reduces the 2D dimension of each feature map (e.g., the X and Y dimensions may each be reduced by half). The pooling operation may be embodied within the DownSampling operation, as indicated by a downward arrow. Several pooling methods, such as max pooling, are known in the art and the specific pooling method is not critical to the present invention. The number of feature maps may double at each pooling, starting with 32 feature maps in the first encoding module (or block), 64 in the second encoding module, and so on. The contracting path thus forms a convolutional network consisting of multiple encoding modules (or stages or blocks). As is typical of convolutional networks, each encoding module may provide at least one convolution stage followed by an activation function (e.g., a rectified linear unit (ReLU) or sigmoid layer), not shown, and a max pooling operation. Generally, an activation function introduces non-linearity into a layer (e.g., to help avoid overfitting issues), receives the results of a layer, and determines whether to "activate" the output (e.g., determines whether the value of a given node meets predefined criteria to have an output forwarded to a next layer/node). In summary, the contracting path generally reduces spatial information while increasing feature information.

The expanding path is similar to a decoder, and among other things, may provide localization and spatial information for the results of the contracting path, despite the down sampling and any max-pooling performed in the contracting stage. The expanding path includes multiple decoding modules, where each decoding module concatenates its current up-converted input with the output of a corresponding encoding module. In this manner, feature and spatial information are combined in the expanding path through a sequence of up-convolutions (e.g., UpSampling or transpose convolutions or deconvolutions) and concatenations with high-resolution features from the contracting path (e.g., via CC1 to CC4). Thus, the output of a deconvolution layer is concatenated with the corresponding (optionally cropped) feature map from the contracting path, followed by two convolutional layers and activation function (with optional batch normalization). The output from the last expanding module in the expanding path may be fed to another processing/training block or layer, such as a classifier block, that may be trained along with the U-Net architecture.

Computing Device/System

Figure 31:
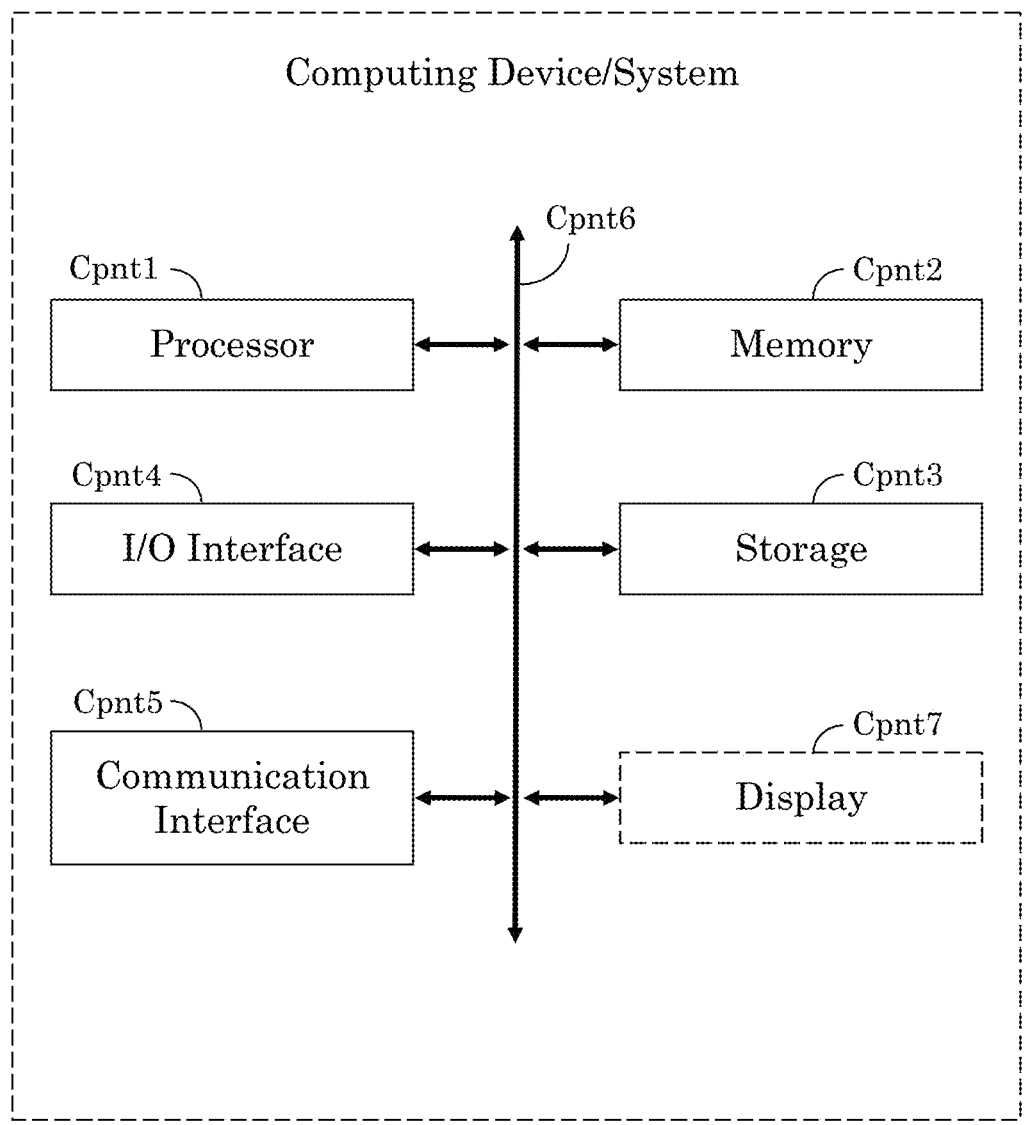
FIG. 31 illustrates an example computer system (or computing device or computer).

FIG. 31 illustrates an example computer system (or computing device or computer device). In some embodiments, one or more computer systems may provide the functionality described or illustrated herein and/or perform one or more steps of one or more methods described or illustrated herein. The computer system may take any suitable physical form. For example, the computer system may be an embedded computer system, a system-on-chip (SOC), a single-board computer system (SBC) (such as, for example, a computer-on-module (COM) or system-on-module (SOM)), a desktop computer system, a laptop or notebook computer system, a mesh of computer systems, a mobile telephone, a personal digital assistant (PDA), a server, a tablet computer system, an augmented/virtual reality device, or a combination of two or more of these. Where appropriate, the computer system may reside in a cloud, which may include one or more cloud components in one or more networks.

In some embodiments, the computer system may include a processor Cpnt1, memory Cpnt2, storage Cpnt3, an input/output (I/O) interface Cpnt4, a communication interface Cpnt5, and a bus Cpnt6. The computer system may optionally also include a display Cpnt7, such as a computer monitor or screen.

Processor Cpnt1 includes hardware for executing instructions, such as those making up a computer program. For example, processor Cpnt1 may be a central processing unit (CPU) or a general-purpose computing on graphics processing unit (GPGPU). Processor Cpnt1 may retrieve (or fetch) the instructions from an internal register, an internal cache, memory Cpnt2, or storage Cpnt3, decode and execute the instructions, and write one or more results to an internal register, an internal cache, memory Cpnt2, or storage Cpnt3. In particular embodiments, processor Cpnt1 may include one or more internal caches for data, instructions, or addresses. Processor Cpnt1 may include one or more instruction caches, one or more data caches, such as to hold data tables. Instructions in the instruction caches may be copies of instructions in memory Cpnt2 or storage Cpnt3, and the instruction caches may speed up retrieval of those instructions by processor Cpnt1. Processor Cpnt1 may include any suitable number of internal registers, and may include one or more arithmetic logic units (ALUs). Processor Cpnt1 may be a multi-core processor; or include one or more processors Cpnt1. Although this disclosure describes and illustrates a particular processor, this disclosure contemplates any suitable processor.

Memory Cpnt2 may include main memory for storing instructions for processor Cpnt1 to execute or to hold interim data during processing. For example, the computer system may load instructions or data (e.g., data tables) from storage Cpnt3 or from another source (such as another computer system) to memory Cpnt2. Processor Cpnt1 may load the instructions and data from memory Cpnt2 to one or more internal register or internal cache. To execute the instructions, processor Cpnt1 may retrieve and decode the instructions from the internal register or internal cache. During or after execution of the instructions, processor Cpnt1 may write one or more results (which may be intermediate or final results) to the internal register, internal cache, memory Cpnt2 or storage Cpnt3. Bus Cpnt6 may include one or more memory buses (which may each include an address bus and a data bus) and may couple processor Cpnt1 to memory Cpnt2 and/or storage Cpnt3. Optionally, one or more memory management unit (MMU) facilitate data transfers between processor Cpnt1 and memory Cpnt2. Memory Cpnt2 (which may be fast, volatile memory) may include random access memory (RAM), such as dynamic RAM (DRAM) or static RAM (SRAM). Storage Cpnt3 may include long-term or mass storage for data or instructions. Storage Cpnt3 may be internal or external to the computer system, and include one or more of a disk drive (e.g., hard-disk drive, HDD, or solid-state drive, SSD), flash memory, ROM, EPROM, optical disc, magneto-optical disc, magnetic tape, Universal Serial Bus (USB)-accessible drive, or other type of non-volatile memory.

I/O interface Cpnt4 may be software, hardware, or a combination of both, and include one or more interfaces (e.g., serial or parallel communication ports) for communication with I/O devices, which may enable communication with a person (e.g., user). For example, I/O devices may include a keyboard, keypad, microphone, monitor, mouse, printer, scanner, speaker, still camera, stylus, tablet, touch screen, trackball, video camera, another suitable I/O device, or a combination of two or more of these.

Communication interface Cpnt5 may provide network interfaces for communication with other systems or networks. Communication interface Cpnt5 may include a Bluetooth interface or other type of packet-based communication. For example, communication interface Cpnt5 may include a network interface controller (NIC) and/or a wireless NIC or a wireless adapter for communicating with a wireless network. Communication interface Cpnt5 may provide communication with a WI-FI network, an ad hoc network, a personal area network (PAN), a wireless PAN (e.g., a Bluetooth WPAN), a local area network (LAN), a wide area network (WAN), a metropolitan area network (MAN), a cellular telephone network (such as, for example, a Global System for Mobile Communications (GSM) network), the Internet, or a combination of two or more of these.

Bus Cpnt6 may provide a communication link between the above-mentioned components of the computing system. For example, bus Cpnt6 may include an Accelerated Graphics Port (AGP) or other graphics bus, an Enhanced Industry Standard Architecture (EISA) bus, a front-side bus (FSB), a HyperTransport (HT) interconnect, an Industry Standard Architecture (ISA) bus, an InfiniBand bus, a low-pin-count (LPC) bus, a memory bus, a Micro Channel Architecture (MCA) bus, a Peripheral Component Interconnect (PCI) bus, a PCI-Express (PCIe) bus, a serial advanced technology attachment (SATA) bus, a Video Electronics Standards Association local (VLB) bus, or other suitable bus or a combination of two or more of these.

Although this disclosure describes and illustrates a particular computer system having a particular number of particular components in a particular arrangement, this disclosure contemplates any suitable computer system having any suitable number of any suitable components in any suitable arrangement.

Herein, a computer-readable non-transitory storage medium or media may include one or more semiconductor-based or other integrated circuits (ICs) (such, as for example, field-programmable gate arrays (FPGAs) or application-specific ICs (ASICs)), hard disk drives (HDDs), hybrid hard drives (HHDs), optical discs, optical disc drives (ODDs), magneto-optical discs, magneto-optical drives, floppy diskettes, floppy disk drives (FDDs), magnetic tapes, solid-state drives (SSDs), RAM-drives, SECURE DIGITAL cards or drives, any other suitable computer-readable non-transitory storage media, or any suitable combination of two or more of these, where appropriate. A computer-readable non-transitory storage medium may be volatile, non-volatile, or a combination of volatile and non-volatile, where appropriate.

While the invention has been described in conjunction with several specific embodiments, it is evident to those skilled in the art that many further alternatives, modifications, and variations will be apparent in light of the foregoing description. Thus, the invention described herein is intended to embrace all such alternatives, modifications, applications and variations as may fall within the spirit and scope of the appended claims.

The invention claimed is:

1. A method comprising:
implementing an electronic processor to perform a set of operations comprising:
extracting depth information from optical coherence tomography (OCT) data, including a superficial vascular plexus at a first depth and a capillary plexus at a second depth greater than the first depth;
identifying a reference capillary region within the capillary plexus having a predefined capillary structural configuration previously defined as being characteristic of one of vein or artery structure;
assigning one of a vein designation or an artery designation to the reference capillary region based on the predefined capillary structural configuration, wherein the predefined capillary structural configuration is based on physical, structural characteristics of capillaries within at least one of an intermediate capillary plexus (ICP) or a deep capillary plexus (DCP);
identifying a vascular connection between the reference capillary region and a first vascular structure within the superficial vascular plexus;
further assigning the vein designation or the artery designation that was assigned to the reference capillary region, to the first vascular structure within the superficial vascular plexus; and
at least one of storing or displaying the vein designation or the artery designation.

2. The method of claim 1, wherein the predefined capillary structural configuration is a local vortex structural configuration, and the reference capillary region is assigned a vein designation.

3. The method of claim 1, wherein the reference capillary region is a region of capillary convergence within the capillary plexus.

4. The method of claim 3, wherein the identified reference capillary region is assigned the vein designation.

5. The method of claim 1, wherein the capillary plexus is at least one of the intermediate capillary plexus (ICP) or the deep capillary plexus (DCP).

6. The method of claim 1, further comprising:
identifying a second vascular structure adjacent to the first vascular structure within the superficial vascular plexus;
wherein the first vascular structure is assigned the vein designation and the second vascular structure is assigned the artery designation.

7. The method of claim 1, wherein the OCT data is an A-scan, B-scan, or C-scan.

8. The method of claim 1, further comprising:
generating at least one depth encoded en face image whose depth encoding differentiates between the superficial vascular plexus and the capillary plexus, the capillary plexus being at least one of the intermediate capillary plexus (ICP) or the deep capillary plexus (DCP).

9. The method of claim 1, wherein the OCT data is a non-depth encoded, en face image, and the depth information is extracted based on the relative widths of the vascular structures of the superficial vascular plexus and capillary structures of the capillary plexus.

10. The method of claim 1, wherein the OCT data comprises OCT angiography data.

11. The method of claim 1, wherein the electronic processor at least partly embodies a neural network.

12. The method of claim 11, further comprising:
extracting, from OCT data samples, OCT-based data examples of reference capillary plexuses having the predefined capillary structural configuration;
wherein the neural network is trained in multiple stages including:
a first stage that receives at least the OCT-based data examples of reference capillary plexuses as training inputs, and uses as training target outputs the OCT-based data samples with one or more labeled reference capillary region having the predefined capillary structural configuration; and
a second stage that receives as a training input the OCT data samples from which the OCT-based data examples are extracted and the output from the first stage, and uses as a training target output the OCT data samples with one or both of veins and arteries labeled.

13. The method of claim 12, wherein the one or both of veins and arteries are labeled on the superficial vascular plexus.

14. The method of claim 12, wherein the training input of the first stage includes an en face image of the capillary plexus, and the corresponding OCT data sample includes an en face image of a slab including both the superficial vascular plexus and the capillary plexus.

15. The method of claim 12, wherein the training input of the first stage includes the same OCT data sample of the second stage, and the OCT data sample includes an en face image of a slab including both the superficial vascular plexus and the capillary plexus.

16. The method of claim 1, further comprising:
   displaying a graphical user interface (GUI) on a screen, the GUI including a vascular image based on the OCT data;
   a user-controlled pointer, wherein in response to the user-controlled pointer selecting a specific vascular branch within the vascular image, the electronic processor determines a relationship between the selected vascular branch and the first vascular structure;
   displaying, on the screen, a vein designation or artery designation for the specific vascular branch based on its relationship to the first vascular structure.

17. The method of claim 16, wherein:
   in response to the determined relationship indicating that the specific vascular branch is part of the first vascular structure, the vein or artery designation of the first vascular structure is displayed for the specific vascular branch; and
   in response to the determined relationship indicating that the specific vascular branch is not part of the first vascular structure and is adjacent to another vascular structure having a vein designation, an artery designation is displayed for the specific vascular branch.

18. The method of claim 1, further comprising:
   displaying a graphical user interface (GUI) on a screen, the GUI including a vascular image based on the OCT data;
   selecting a specific vascular branch within the vascular image by use of a user-controlled pointer;
   wherein:
   the electronic processor performs the set of operations in response to the user-controlled pointer selecting the specific vascular branch; and
   the specific vascular branch corresponds to the first vascular structure.

19. A system for identifying a vein or artery within optical coherence tomography (OCT) data obtained from an eye, comprising:
   an OCT system for collecting the OCT data;
   an electronic processor; and
   a non-transitory computer readable media containing computer executable instructions that causes the electronic processor to:
      extract depth information from the OCT data, including a superficial vascular plexus at a first depth and a capillary plexus at a second depth deeper than the first depth;
      identify a reference capillary region within the capillary plexus characterized by a predefined structural configuration previously defined as being characteristic of one of vein or artery structure;
      assign one of a vein designation or an artery designation to the reference capillary region based on the predefined capillary structural configuration, wherein the predefined capillary structural configuration is based on physical, structural characteristics of capillaries within at least one of an intermediate capillary plexus (ICP) or a deep capillary plexus (DCP);
      identify a vascular connection between the reference capillary region and a first vascular structure within the superficial vascular plexus; and
      assign the vein designation or the artery designation that was assigned to the reference capillary region, to the first vascular structure within the superficial vascular plexus.

20. The system of claim 19, wherein the predefined structural configuration comprises a local vortex structural configuration of the capillaries or a local region of capillary convergence within the capillary plexus.

21. The system of claim 20, wherein the second depth corresponds to an intermediate capillary plexus or a deep capillary plexus of an eye.

22. The system of claim 21, wherein the OCT data is OCT angiography (OCTA) data.

23. A system comprising:
   an electronic processor configured to execute a set of operations including:
      extracting depth information from optical coherence tomography (OCT) based data, including a superficial vascular plexus at a first depth and a capillary plexus at a second depth deeper than the first depth, the capillary plexus including at least one of an intermediate capillary plexus (ICP) or a deep capillary plexus (DCP);
      identifying a reference capillary region, within the capillary plexus, having a capillary structural configuration characterized by a local vortex structural configuration, wherein the capillary structural configuration is based on physical, structural characteristics of capillaries within at least one of the intermediate capillary plexus (ICP) or the deep capillary plexus (DCP);
      assigning a vein designation to the reference capillary region;
      identifying a vascular connection between the reference capillary region and a first vascular structure within the superficial vascular plexus;
      assigning the vein designation to the first vascular structure within the superficial vascular plexus; and
      storing or displaying the vein designation of at least one of the reference capillary region and the first vascular structure.

24. The system of claim 23, wherein the set of operations further includes:
   identifying a second vascular structure within the superficial vascular plexus, the second vascular structure being adjacent to the first vascular structure and lacking a vascular connection to the reference capillary region; and
   assigning an artery designation to the second vascular structure.

25. The system of claim 23, wherein the OCT based data is a non-depth encoded, en face image, and the depth information is extracted based on the relative widths of the vascular structures of the superficial vascular plexus and the capillary structures of the capillary plexus.

* * * * *